(12) United States Patent
Frangineas, Jr.

(10) Patent No.: US 11,154,418 B2
(45) Date of Patent: Oct. 26, 2021

(54) VASCULAR TREATMENT SYSTEMS, COOLING DEVICES, AND METHODS FOR COOLING VASCULAR STRUCTURES

(71) Applicant: Zeltiq Aesthestics, Inc., Pleasanton, CA (US)

(72) Inventor: George Frangineas, Jr., Fremont, CA (US)

(73) Assignee: Zeltiq Aesthetics, Inc., Pleasanton, CA (US)

( * ) Notice: Subject to any disclaimer, the term of this patent is extended or adjusted under 35 U.S.C. 154(b) by 169 days.

(21) Appl. No.: 15/296,853

(22) Filed: Oct. 18, 2016

(65) Prior Publication Data

US 2017/0105869 A1    Apr. 20, 2017

Related U.S. Application Data

(60) Provisional application No. 62/243,529, filed on Oct. 19, 2015.

(51) Int. Cl.
*A61F 7/00* (2006.01)
*A61B 18/02* (2006.01)
*A61B 18/00* (2006.01)

(52) U.S. Cl.
CPC ............. *A61F 7/007* (2013.01); *A61B 18/02* (2013.01); *A61B 2018/00404* (2013.01);
(Continued)

(58) Field of Classification Search
CPC ............ A61B 18/02; A61B 2018/0237; A61B 2018/0005; A61B 2018/00458; A61B 2017/00756; A61B 2018/00404; A61B 2018/00702; A61B 2018/00791; A61B 2018/00988; A61F 7/007; A61F 2007/0093; A61F 2007/029; A61F 2007/0052;
(Continued)

(56) References Cited

U.S. PATENT DOCUMENTS 681,806 A    9/1901  Mignault et al.
889,810 A    6/1908  Robinson et al.
(Continued)

FOREIGN PATENT DOCUMENTS

AU    2011253768 A1    6/2012
CA    2441489 A1       3/2005
(Continued)

OTHER PUBLICATIONS

Aguilar et al., "Modeling Cryogenic Spray Temperature and Evaporation Rate Based on Single-Droplet Analysis," Eighth International Conference on Liquid Atomization and Spray Systems, Pasadena, CA, USA, Jul. 2000, 7 pages.
(Continued)

*Primary Examiner* — Eun Hwa Kim
*Assistant Examiner* — Adam Z Minchella
(74) *Attorney, Agent, or Firm* — Perkins Coie LLP

(57) ABSTRACT

Treatment systems, methods, and apparatuses for improving the appearance of skin and other treatments are described. Aspects of the technology are directed to improving the appearance of skin by reducing a vascular structure. A non-invasive cooling device can cover and cool the vascular structure to affect the blood vessels of the vascular structure.

14 Claims, 10 Drawing Sheets

(52) U.S. Cl.
CPC ............... *A61B 2018/00458* (2013.01); *A61B 2018/00702* (2013.01); *A61B 2018/00791* (2013.01); *A61B 2018/00988* (2013.01); *A61B 2018/0237* (2013.01); *A61F 2007/0052* (2013.01); *A61F 2007/0071* (2013.01); *A61F 2007/0075* (2013.01); *A61F 2007/0087* (2013.01); *A61F 2007/0093* (2013.01); *A61F 2007/0095* (2013.01)

(58) Field of Classification Search
CPC ...... A61F 2007/0071; A61F 2007/0075; A61F 2007/0087; A61F 2007/0095
See application file for complete search history.

(56) References Cited

U.S. PATENT DOCUMENTS

| | | |
|---|---|---|
| 1,093,868 A | 4/1914 | Leighty |
| 2,516,491 A | 7/1950 | Swastek |
| 2,521,780 A | 9/1950 | Dodd et al. |
| 2,726,658 A | 12/1955 | Chessey |
| 2,766,619 A | 10/1956 | Tribus et al. |
| 2,851,602 A | 9/1958 | Cramwinckel et al. |
| 3,093,135 A | 6/1963 | Hirschhorn |
| 3,132,688 A | 5/1964 | Nowak |
| 3,133,539 A | 5/1964 | Eidus et al. |
| 3,282,267 A | 11/1966 | Eidus |
| 3,341,230 A | 9/1967 | Louis |
| 3,502,080 A | 3/1970 | Hirschhorn |
| 3,566,871 A | 3/1971 | Richter et al. |
| 3,587,577 A | 6/1971 | Zubkov et al. |
| 3,591,645 A | 7/1971 | Selwitz |
| 3,692,338 A | 9/1972 | Nick |
| 3,703,897 A | 11/1972 | Mack et al. |
| 3,710,784 A | 1/1973 | Taylor |
| 3,786,814 A | 1/1974 | Armao |
| 3,827,436 A | 8/1974 | Andera et al. |
| 3,942,519 A | 3/1976 | Shock |
| 3,948,269 A | 4/1976 | Zimmer |
| 3,986,385 A | 10/1976 | Johnston et al. |
| 3,993,053 A | 11/1976 | Grossan |
| 4,002,221 A | 1/1977 | Buchalter |
| 4,008,910 A | 2/1977 | Roche |
| 4,026,299 A | 5/1977 | Sauder |
| 4,140,130 A | 2/1979 | Storm |
| 4,149,529 A | 4/1979 | Copeland et al. |
| 4,178,429 A | 12/1979 | Scheffer |
| 4,202,336 A | 5/1980 | Van Gerven |
| 4,266,043 A | 5/1981 | Fujii et al. |
| 4,269,068 A | 5/1981 | Molina |
| 4,381,009 A | 4/1983 | Del Bon |
| 4,396,011 A | 8/1983 | Mack et al. |
| 4,459,854 A | 7/1984 | Richardson et al. |
| 4,470,263 A | 9/1984 | Lehovec et al. |
| 4,483,341 A | 11/1984 | Witteles |
| 4,528,979 A | 7/1985 | Marchenko et al. |
| 4,531,524 A | 7/1985 | Mioduski |
| 4,548,212 A | 10/1985 | Leung |
| 4,555,313 A | 11/1985 | Duchane et al. |
| 4,585,002 A | 4/1986 | Kissin |
| 4,603,076 A | 7/1986 | Bowditch et al. |
| 4,614,191 A | 9/1986 | Perler et al. |
| 4,644,955 A | 2/1987 | Mioduski |
| 4,664,110 A | 5/1987 | Schanzlin |
| 4,700,701 A | 10/1987 | Montaldi |
| 4,718,429 A | 1/1988 | Smidt |
| 4,741,338 A | 5/1988 | Miyamae |
| 4,758,217 A | 7/1988 | Gueret |
| 4,764,463 A | 8/1988 | Mason et al. |
| 4,802,475 A | 2/1989 | Weshahy |
| 4,832,022 A | 5/1989 | Tjulkov et al. |
| 4,846,176 A | 7/1989 | Golden |
| 4,850,340 A | 7/1989 | Onishi |
| 4,869,250 A | 9/1989 | Bitterly |
| 4,880,564 A | 11/1989 | Abel et al. |
| 4,905,697 A | 3/1990 | Heggs et al. |
| 4,906,463 A | 3/1990 | Cleary et al. |
| 4,930,317 A | 6/1990 | Klein |
| 4,935,345 A | 6/1990 | Guilbeau et al. |
| 4,961,422 A | 10/1990 | Marchosky et al. |
| 4,962,761 A | 10/1990 | Golden |
| 4,990,144 A | 2/1991 | Blott et al. |
| 5,007,433 A | 4/1991 | Hermsdoerffer et al. |
| 5,018,521 A | 5/1991 | Campbell et al. |
| 5,024,650 A | 6/1991 | Hagiwara et al. |
| 5,065,752 A | 11/1991 | Sessions et al. |
| 5,069,208 A | 12/1991 | Noppel et al. |
| 5,084,671 A | 1/1992 | Miyata et al. |
| 5,108,390 A | 4/1992 | Potocky et al. |
| 5,119,674 A | 6/1992 | Nielsen |
| 5,139,496 A | 8/1992 | Hed |
| 5,143,063 A | 9/1992 | Fellner |
| 5,148,804 A | 9/1992 | Hill et al. |
| 5,158,070 A | 10/1992 | Dory |
| 5,160,312 A | 11/1992 | Voelkel |
| 5,169,384 A | 12/1992 | Bosniak et al. |
| 5,197,466 A | 3/1993 | Marchosky et al. |
| 5,207,674 A | 5/1993 | Hamilton |
| 5,221,726 A | 6/1993 | Dabi et al. |
| 5,264,234 A | 11/1993 | Windhab et al. |
| 5,277,030 A | 1/1994 | Miller |
| 5,314,423 A | 5/1994 | Seney et al. |
| 5,327,886 A | 7/1994 | Chiu |
| 5,330,745 A * | 7/1994 | McDow ............ A61B 18/0218 424/43 |
| 5,333,460 A | 8/1994 | Lewis et al. |
| 5,334,131 A | 8/1994 | Omandam et al. |
| 5,336,616 A | 8/1994 | Livesey et al. |
| 5,339,541 A | 8/1994 | Owens |
| 5,342,617 A | 8/1994 | Gold et al. |
| 5,351,677 A | 10/1994 | Kami et al. |
| 5,358,467 A | 10/1994 | Milstein et al. |
| 5,362,966 A | 11/1994 | Rosenthal et al. |
| 5,363,347 A | 11/1994 | Nguyen |
| 5,372,608 A | 12/1994 | Johnson |
| 5,386,837 A | 2/1995 | Sterzer |
| 5,411,541 A | 5/1995 | Bell et al. |
| 5,427,772 A | 6/1995 | Hagan et al. |
| 5,433,717 A | 7/1995 | Rubinsky et al. |
| 5,456,703 A | 10/1995 | Beeuwkes, III et al. |
| 5,472,416 A | 12/1995 | Blugerman et al. |
| 5,486,207 A | 1/1996 | Mahawili |
| 5,497,596 A | 3/1996 | Zatkulak |
| 5,501,655 A | 3/1996 | Rolt et al. |
| 5,505,726 A | 4/1996 | Meserol |
| 5,505,730 A | 4/1996 | Edwards et al. |
| 5,507,790 A | 4/1996 | Weiss |
| 5,514,105 A | 5/1996 | Goodman, Jr. et al. |
| 5,514,170 A | 5/1996 | Mauch |
| 5,516,505 A | 5/1996 | McDow |
| 5,531,742 A | 7/1996 | Barken |
| 5,558,376 A | 9/1996 | Woehl |
| 5,562,604 A | 10/1996 | Yablon et al. |
| 5,571,801 A | 11/1996 | Segall et al. |
| 5,575,812 A | 11/1996 | Owens et al. |
| 5,603,221 A | 2/1997 | Maytal |
| 5,628,769 A | 5/1997 | Saringer |
| 5,634,890 A | 6/1997 | Morris |
| 5,634,940 A | 6/1997 | Panyard |
| 5,647,051 A | 7/1997 | Neer |
| 5,647,868 A | 7/1997 | Chinn |
| 5,650,450 A | 7/1997 | Lovette et al. |
| 5,651,773 A | 7/1997 | Perry et al. |
| 5,654,279 A | 8/1997 | Rubinsky et al. |
| 5,654,546 A | 8/1997 | Lindsay et al. |
| 5,660,836 A | 8/1997 | Knowlton et al. |
| 5,665,053 A | 9/1997 | Jacobs |
| 5,672,172 A | 9/1997 | Zupkas |
| 5,700,284 A | 12/1997 | Owens et al. |
| 5,725,483 A | 3/1998 | Podolsky |
| 5,733,280 A | 3/1998 | Avitall |
| 5,741,248 A | 4/1998 | Stern et al. |
| 5,746,702 A | 5/1998 | Gelfget et al. |
| 5,746,736 A | 5/1998 | Tankovich |

(56) References Cited

U.S. PATENT DOCUMENTS

| | | |
|---|---|---|
| 5,755,663 A | 5/1998 | Larsen et al. |
| 5,755,753 A | 5/1998 | Knowlton et al. |
| 5,755,755 A | 5/1998 | Panyard |
| 5,759,182 A | 6/1998 | Varney et al. |
| 5,759,764 A | 6/1998 | Polovina et al. |
| 5,769,879 A | 6/1998 | Richards et al. |
| 5,785,955 A | 7/1998 | Fischer |
| 5,792,080 A | 8/1998 | Ookawa et al. |
| 5,800,490 A | 9/1998 | Patz et al. |
| 5,802,865 A | 9/1998 | Strauss |
| 5,814,040 A | 9/1998 | Nelson et al. |
| 5,817,050 A | 10/1998 | Klein et al. |
| 5,817,149 A | 10/1998 | Owens et al. |
| 5,817,150 A | 10/1998 | Owens et al. |
| 5,830,208 A | 11/1998 | Muller et al. |
| 5,833,685 A | 11/1998 | Tortal et al. |
| 5,844,013 A | 12/1998 | Kenndoff et al. |
| 5,853,364 A | 12/1998 | Baker, Jr. et al. |
| 5,865,841 A | 2/1999 | Kolen et al. |
| 5,871,524 A | 2/1999 | Knowlton |
| 5,871,526 A | 2/1999 | Gibbs et al. |
| 5,885,211 A | 3/1999 | Eppstein et al. |
| 5,891,617 A | 4/1999 | Watson et al. |
| 5,895,418 A | 4/1999 | Saringer |
| 5,901,707 A * | 5/1999 | Gon.cedilla.alves .. A61B 90/04 128/853 |
| 5,902,256 A | 5/1999 | Benaron |
| 5,919,219 A | 7/1999 | Knowlton et al. |
| 5,944,748 A | 8/1999 | Mager et al. |
| 5,948,011 A | 9/1999 | Knowlton et al. |
| 5,954,680 A | 9/1999 | Augustine et al. |
| 5,964,092 A | 10/1999 | Tozuka et al. |
| 5,964,749 A | 10/1999 | Eckhouse et al. |
| 5,967,976 A | 10/1999 | Larsen et al. |
| 5,980,561 A | 11/1999 | Kolen et al. |
| 5,986,167 A | 11/1999 | Arteman et al. |
| 5,989,286 A | 11/1999 | Owens et al. |
| 5,997,530 A | 12/1999 | Nelson et al. |
| 6,017,337 A | 1/2000 | Pira |
| 6,023,932 A | 2/2000 | Johnston |
| 6,032,675 A | 3/2000 | Rubinsky |
| 6,039,694 A | 3/2000 | Larson et al. |
| 6,041,787 A | 3/2000 | Rubinsky |
| 6,047,215 A | 4/2000 | McClure et al. |
| 6,049,927 A | 4/2000 | Thomas et al. |
| 6,051,159 A | 4/2000 | Hao et al. |
| 6,071,239 A | 6/2000 | Cribbs et al. |
| 6,074,415 A | 6/2000 | Der Ovanesian |
| 6,093,230 A | 7/2000 | Johnson et al. |
| 6,102,885 A | 8/2000 | Bass |
| 6,104,952 A | 8/2000 | Tu et al. |
| 6,104,959 A | 8/2000 | Spertell et al. |
| 6,106,517 A | 8/2000 | Zupkas |
| 6,113,558 A | 9/2000 | Rosenschein et al. |
| 6,113,559 A | 9/2000 | Klopotek |
| 6,113,626 A | 9/2000 | Clifton et al. |
| 6,120,519 A | 9/2000 | Weber et al. |
| 6,139,544 A | 10/2000 | Mikus et al. |
| 6,150,148 A | 11/2000 | Nanda et al. |
| 6,151,735 A | 11/2000 | Koby et al. |
| 6,152,952 A | 11/2000 | Owens et al. |
| 6,171,301 B1 | 1/2001 | Nelson et al. |
| 6,180,867 B1 | 1/2001 | Hedengren et al. |
| 6,226,996 B1 | 5/2001 | Weber et al. |
| 6,241,753 B1 | 6/2001 | Knowlton |
| 6,264,649 B1 | 7/2001 | Whitcroft et al. |
| 6,273,884 B1 | 8/2001 | Altshuler et al. |
| 6,290,988 B1 | 9/2001 | Van Vilsteren et al. |
| 6,311,090 B1 | 10/2001 | Knowlton |
| 6,311,497 B1 | 11/2001 | Chung |
| 6,312,453 B1 | 11/2001 | Stefanile et al. |
| 6,350,276 B1 | 2/2002 | Knowlton |
| 6,354,297 B1 | 3/2002 | Eiseman |
| 6,357,907 B1 | 3/2002 | Cleveland et al. |
| 6,375,673 B1 | 4/2002 | Clifton et al. |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,401,722 B1 | 6/2002 | Krag |
| 6,405,090 B1 | 6/2002 | Knowlton |
| 6,413,255 B1 | 7/2002 | Stern |
| 6,425,912 B1 | 7/2002 | Knowlton |
| 6,426,445 B1 | 7/2002 | Young et al. |
| 6,430,446 B1 | 8/2002 | Knowlton |
| 6,430,956 B1 | 8/2002 | Haas et al. |
| 6,438,424 B1 | 8/2002 | Knowlton |
| 6,438,954 B1 | 8/2002 | Goetz et al. |
| 6,438,964 B1 | 8/2002 | Giblin |
| 6,453,202 B1 | 9/2002 | Knowlton |
| 6,458,888 B1 | 10/2002 | Hood et al. |
| 6,461,378 B1 | 10/2002 | Knowlton |
| 6,470,216 B1 | 10/2002 | Knowlton |
| 6,471,693 B1 | 10/2002 | Carroll et al. |
| 6,475,211 B2 | 11/2002 | Chess et al. |
| 6,478,811 B1 | 11/2002 | Dobak, III et al. |
| 6,494,844 B1 | 12/2002 | Van Bladel et al. |
| 6,497,721 B2 | 12/2002 | Ginsburg et al. |
| 6,508,831 B1 | 1/2003 | Kushnir |
| 6,514,244 B2 | 2/2003 | Pope et al. |
| 6,519,964 B2 | 2/2003 | Bieberich |
| 6,523,354 B1 | 2/2003 | Tolbert |
| 6,527,765 B2 | 3/2003 | Kelman et al. |
| 6,527,798 B2 | 3/2003 | Ginsburg et al. |
| 6,544,248 B1 | 4/2003 | Bass |
| 6,547,811 B1 | 4/2003 | Becker et al. |
| 6,548,297 B1 | 4/2003 | Kuri-Harcuch et al. |
| 6,551,255 B2 | 4/2003 | Van Bladel et al. |
| 6,551,341 B2 | 4/2003 | Boylan et al. |
| 6,551,348 B1 | 4/2003 | Blalock et al. |
| 6,551,349 B2 | 4/2003 | Lasheras et al. |
| 6,569,189 B1 | 5/2003 | Augustine et al. |
| 6,585,652 B2 | 7/2003 | Lang et al. |
| 6,592,577 B2 | 7/2003 | Abboud et al. |
| 6,605,080 B1 | 8/2003 | Altshuler et al. |
| 6,607,498 B2 | 8/2003 | Eshel |
| 6,620,187 B2 | 9/2003 | Carson et al. |
| 6,620,188 B1 | 9/2003 | Ginsburg et al. |
| 6,620,189 B1 | 9/2003 | Machold et al. |
| 6,623,430 B1 | 9/2003 | Slayton et al. |
| 6,626,854 B2 | 9/2003 | Friedman et al. |
| 6,632,219 B1 | 10/2003 | Baranov et al. |
| 6,635,053 B1 | 10/2003 | Lalonde et al. |
| 6,643,535 B2 | 11/2003 | Damasco et al. |
| 6,645,162 B2 | 11/2003 | Friedman et al. |
| 6,645,229 B2 | 11/2003 | Matsumura et al. |
| 6,645,232 B2 | 11/2003 | Carson |
| 6,648,904 B2 | 11/2003 | Altshuler et al. |
| 6,656,208 B2 | 12/2003 | Grahn et al. |
| 6,660,027 B2 | 12/2003 | Gruszecki et al. |
| 6,662,054 B2 | 12/2003 | Kreindel et al. |
| 6,682,550 B2 | 1/2004 | Clifton et al. |
| 6,685,731 B2 | 2/2004 | Kushnir et al. |
| 6,694,170 B1 | 2/2004 | Mikus et al. |
| 6,695,874 B2 | 2/2004 | Machold et al. |
| 6,697,670 B2 | 2/2004 | Chornenky |
| 6,699,237 B2 | 3/2004 | Weber et al. |
| 6,699,266 B2 | 3/2004 | Lachenbruch et al. |
| 6,699,267 B2 | 3/2004 | Voorhees et al. |
| 6,718,785 B2 | 4/2004 | Bieberich |
| 6,741,895 B1 | 5/2004 | Gafni et al. |
| 6,743,222 B2 | 6/2004 | Durkin et al. |
| 6,746,474 B2 | 6/2004 | Saadat |
| 6,749,624 B2 | 6/2004 | Knowlton |
| 6,753,182 B1 | 6/2004 | Kadkade et al. |
| 6,764,493 B1 | 7/2004 | Weber et al. |
| 6,764,502 B2 | 7/2004 | Bieberich |
| 6,789,545 B2 | 9/2004 | Littrup et al. |
| 6,795,728 B2 | 9/2004 | Chornenky et al. |
| 6,820,961 B2 | 11/2004 | Johnson |
| 6,821,274 B2 | 11/2004 | McHale et al. |
| 6,840,955 B2 | 1/2005 | Ein |
| 6,849,075 B2 | 2/2005 | Bertolero et al. |

(56) References Cited

U.S. PATENT DOCUMENTS

| | | |
|---|---|---|
| 6,878,144 B2 | 4/2005 | Altshuler et al. |
| 6,889,090 B2 | 5/2005 | Kreindel |
| 6,892,099 B2 | 5/2005 | Jaafar et al. |
| 6,904,956 B2 | 6/2005 | Noel |
| 6,918,903 B2 | 7/2005 | Bass |
| 6,927,316 B1 | 8/2005 | Faries, Jr. et al. |
| 6,942,022 B2 | 9/2005 | Blangetti et al. |
| 6,945,942 B2 | 9/2005 | Van Bladel et al. |
| 6,948,903 B2 | 9/2005 | Ablabutyan et al. |
| 6,969,399 B2 | 11/2005 | Schock et al. |
| 7,005,558 B1 | 2/2006 | Johansson et al. |
| 7,006,874 B2 | 2/2006 | Knowlton et al. |
| 7,022,121 B2 | 4/2006 | Stern et al. |
| 7,037,326 B2 | 5/2006 | Lee |
| 7,054,685 B2 | 5/2006 | Dimmer et al. |
| 7,060,061 B2 | 6/2006 | Altshuler et al. |
| 7,077,858 B2 | 7/2006 | Fletcher et al. |
| 7,081,111 B2 | 7/2006 | Svaasand et al. |
| 7,083,612 B2 | 8/2006 | Littrup et al. |
| 7,096,204 B1 | 8/2006 | Chen et al. |
| 7,112,712 B1 | 9/2006 | Ancell |
| 7,115,123 B2 | 10/2006 | Knowlton et al. |
| 7,141,049 B2 | 11/2006 | Stern et al. |
| 7,183,360 B2 | 2/2007 | Daniel et al. |
| 7,189,252 B2 | 3/2007 | Krueger |
| 7,192,426 B2 | 3/2007 | Baust et al. |
| 7,204,832 B2 | 4/2007 | Altshuler et al. |
| 7,220,778 B2 | 5/2007 | Anderson et al. |
| 7,229,436 B2 | 6/2007 | Stern et al. |
| 7,258,674 B2 | 8/2007 | Cribbs et al. |
| 7,267,675 B2 | 9/2007 | Stern et al. |
| 7,276,058 B2 | 10/2007 | Altshuler et al. |
| 7,318,821 B2 | 1/2008 | Lalonde et al. |
| 7,331,951 B2 | 2/2008 | Eshel et al. |
| 7,347,855 B2 | 3/2008 | Eshel et al. |
| 7,367,341 B2 | 5/2008 | Anderson et al. |
| 7,532,201 B2 | 5/2009 | Quistgaard et al. |
| 7,572,268 B2 | 8/2009 | Babaev |
| 7,604,632 B2 | 10/2009 | Howlett et al. |
| 7,613,523 B2 | 11/2009 | Eggers et al. |
| 7,615,016 B2 | 11/2009 | Barthe et al. |
| 7,713,266 B2 | 5/2010 | Elkins et al. |
| 7,780,656 B2 | 8/2010 | Tankovich |
| 7,799,018 B2 | 9/2010 | Goulko |
| 7,824,437 B1 | 11/2010 | Saunders |
| 7,828,831 B1 | 11/2010 | Tanhehco et al. |
| 7,850,683 B2 | 12/2010 | Elkins et al. |
| 7,854,754 B2 | 12/2010 | Ting et al. |
| 7,862,558 B2 | 1/2011 | Elkins et al. |
| RE42,277 E | 4/2011 | Jaafar et al. |
| 7,938,824 B2 | 5/2011 | Chornenky et al. |
| 7,959,657 B1 | 6/2011 | Harsy et al. |
| 7,963,959 B2 | 6/2011 | Da Silva et al. |
| 7,967,763 B2 | 6/2011 | Deem et al. |
| 7,993,330 B2 | 8/2011 | Goulko |
| 7,998,137 B2 | 8/2011 | Elkins et al. |
| RE42,835 E | 10/2011 | Chornenky et al. |
| RE43,009 E | 12/2011 | Chornenky et al. |
| 8,133,180 B2 | 3/2012 | Slayton et al. |
| 8,133,191 B2 | 3/2012 | Rosenberg et al. |
| 8,192,474 B2 | 6/2012 | Levinson |
| 8,246,611 B2 | 8/2012 | Paithankar et al. |
| 8,275,442 B2 | 9/2012 | Allison |
| 8,285,390 B2 | 10/2012 | Levinson et al. |
| 8,333,700 B1 | 12/2012 | Barthe et al. |
| 8,337,539 B2 | 12/2012 | Ting et al. |
| 8,366,622 B2 | 2/2013 | Slayton et al. |
| 8,372,130 B2 | 2/2013 | Young et al. |
| 8,397,518 B1 | 3/2013 | Vistakula et al. |
| 8,414,631 B2 | 4/2013 | Quisenberry et al. |
| 8,433,400 B2 | 4/2013 | Prushinskaya et al. |
| 8,506,486 B2 | 8/2013 | Slayton et al. |
| 8,523,775 B2 | 9/2013 | Barthe et al. |
| 8,523,791 B2 | 9/2013 | Castel |
| 8,523,927 B2 | 9/2013 | Levinson et al. |
| 8,535,228 B2 | 9/2013 | Slayton et al. |
| 8,603,073 B2 | 12/2013 | Allison |
| 8,636,665 B2 | 1/2014 | Slayton et al. |
| 8,641,622 B2 | 2/2014 | Barthe et al. |
| 8,663,112 B2 | 3/2014 | Slayton et al. |
| 8,672,848 B2 | 3/2014 | Slayton et al. |
| 8,676,332 B2 | 3/2014 | Fahey |
| 8,690,778 B2 | 4/2014 | Slayton et al. |
| 8,690,779 B2 | 4/2014 | Slayton et al. |
| 8,690,780 B2 | 4/2014 | Slayton et al. |
| 8,702,774 B2 | 4/2014 | Baker et al. |
| 8,758,215 B2 | 6/2014 | Legendre et al. |
| 8,764,693 B1 | 7/2014 | Graham et al. |
| 8,834,547 B2 | 9/2014 | Anderson et al. |
| 9,149,322 B2 | 10/2015 | Knowlton |
| 9,855,166 B2 * | 1/2018 | Anderson ............ A61B 18/02 |
| 2001/0005791 A1 | 6/2001 | Ginsburg et al. |
| 2001/0007952 A1 | 7/2001 | Shimizu |
| 2001/0023364 A1 | 9/2001 | Ahn |
| 2001/0031459 A1 | 10/2001 | Fahy et al. |
| 2001/0039439 A1 | 11/2001 | Elkins et al. |
| 2001/0045104 A1 | 11/2001 | Bailey, Sr. et al. |
| 2001/0047196 A1 | 11/2001 | Ginsburg et al. |
| 2002/0026226 A1 | 2/2002 | Ein |
| 2002/0032473 A1 | 3/2002 | Kushnir et al. |
| 2002/0042607 A1 | 4/2002 | Palmer et al. |
| 2002/0049483 A1 | 4/2002 | Knowlton |
| 2002/0058975 A1 | 5/2002 | Bieberich |
| 2002/0062142 A1 | 5/2002 | Knowlton |
| 2002/0068338 A1 | 6/2002 | Nanda et al. |
| 2002/0068874 A1 | 6/2002 | Zuckerwar et al. |
| 2002/0082668 A1 | 6/2002 | Ingman |
| 2002/0103520 A1 | 8/2002 | Latham |
| 2002/0107558 A1 | 8/2002 | Clifton et al. |
| 2002/0117293 A1 | 8/2002 | Campbell |
| 2002/0120315 A1 | 8/2002 | Furuno et al. |
| 2002/0128648 A1 | 9/2002 | Weber et al. |
| 2002/0151830 A1 | 10/2002 | Kahn |
| 2002/0151887 A1 | 10/2002 | Stern et al. |
| 2002/0156509 A1 | 10/2002 | Cheung |
| 2002/0161357 A1 * | 10/2002 | Anderson ............ A61B 18/203 606/9 |
| 2002/0188286 A1 | 12/2002 | Quijano et al. |
| 2002/0198518 A1 | 12/2002 | Mikus et al. |
| 2003/0032900 A1 | 2/2003 | Ella |
| 2003/0044764 A1 | 3/2003 | Soane et al. |
| 2003/0055414 A1 | 3/2003 | Altshuler et al. |
| 2003/0062040 A1 | 4/2003 | Lurie et al. |
| 2003/0069618 A1 | 4/2003 | Smith, III et al. |
| 2003/0077326 A1 | 4/2003 | Newton et al. |
| 2003/0077329 A1 | 4/2003 | Kipp et al. |
| 2003/0079488 A1 | 5/2003 | Bieberich |
| 2003/0100936 A1 | 5/2003 | Altshuler et al. |
| 2003/0109908 A1 | 6/2003 | Lachenbruch et al. |
| 2003/0109910 A1 | 6/2003 | Lachenbruch et al. |
| 2003/0109911 A1 | 6/2003 | Lachenbruch et al. |
| 2003/0109912 A1 | 6/2003 | Joye et al. |
| 2003/0114885 A1 | 6/2003 | Nova et al. |
| 2003/0120268 A1 | 6/2003 | Bertolero et al. |
| 2003/0125649 A1 | 7/2003 | McIntosh et al. |
| 2003/0187488 A1 | 10/2003 | Kreindel et al. |
| 2003/0199226 A1 | 10/2003 | Sommer et al. |
| 2003/0199859 A1 | 10/2003 | Altshuler et al. |
| 2003/0220594 A1 | 11/2003 | Halvorson et al. |
| 2003/0220635 A1 | 11/2003 | Knowlton et al. |
| 2003/0220674 A1 * | 11/2003 | Anderson ............ A61B 5/415 607/96 |
| 2003/0236487 A1 | 12/2003 | Knowlton |
| 2004/0002705 A1 | 1/2004 | Knowlton et al. |
| 2004/0006328 A1 | 1/2004 | Anderson |
| 2004/0009936 A1 | 1/2004 | Tang et al. |
| 2004/0024437 A1 | 2/2004 | Machold et al. |
| 2004/0030332 A1 | 2/2004 | Knowlton et al. |
| 2004/0034341 A1 | 2/2004 | Altshuler et al. |
| 2004/0039312 A1 | 2/2004 | Hillstead et al. |
| 2004/0044384 A1 | 3/2004 | Leber et al. |
| 2004/0049178 A1 | 3/2004 | Abboud et al. |
| 2004/0073079 A1 * | 4/2004 | Altshuler ............ A61N 5/0616 600/1 |

(56) References Cited

U.S. PATENT DOCUMENTS

| | | |
|---|---|---|
| 2004/0074629 A1 | 4/2004 | Noel |
| 2004/0077977 A1 | 4/2004 | Ella et al. |
| 2004/0082886 A1 | 4/2004 | Timpson |
| 2004/0093042 A1 | 5/2004 | Altshuler et al. |
| 2004/0104012 A1 | 6/2004 | Zhou et al. |
| 2004/0106867 A1 | 6/2004 | Eshel et al. |
| 2004/0133251 A1 | 7/2004 | Altshuler et al. |
| 2004/0162596 A1 | 8/2004 | Altshuler et al. |
| 2004/0176667 A1 | 9/2004 | Mihai et al. |
| 2004/0186535 A1 | 9/2004 | Knowlton |
| 2004/0199226 A1 | 10/2004 | Shadduck |
| 2004/0206365 A1 | 10/2004 | Knowlton |
| 2004/0210214 A1 | 10/2004 | Knowlton |
| 2004/0210287 A1 | 10/2004 | Greene |
| 2004/0215294 A1 | 10/2004 | Littrup et al. |
| 2004/0249427 A1 | 12/2004 | Nabilsi et al. |
| 2004/0259855 A1 | 12/2004 | Anderson et al. |
| 2004/0260209 A1 | 12/2004 | Ella et al. |
| 2004/0260210 A1 | 12/2004 | Ella et al. |
| 2004/0260211 A1 | 12/2004 | Maalouf |
| 2004/0267339 A1 | 12/2004 | Yon et al. |
| 2005/0010197 A1 | 1/2005 | Lau et al. |
| 2005/0033957 A1 | 2/2005 | Enokida |
| 2005/0049526 A1 | 3/2005 | Baer |
| 2005/0049543 A1 | 3/2005 | Anderson et al. |
| 2005/0049661 A1 | 3/2005 | Koffroth |
| 2005/0065531 A1* | 3/2005 | Cohen ............... A61B 18/203 606/88 |
| 2005/0113725 A1 | 5/2005 | Masuda |
| 2005/0143781 A1 | 6/2005 | Carbunaru et al. |
| 2005/0145372 A1 | 7/2005 | Noel |
| 2005/0149153 A1 | 7/2005 | Nakase et al. |
| 2005/0154314 A1 | 7/2005 | Quistgaard |
| 2005/0154431 A1 | 7/2005 | Quistgaard et al. |
| 2005/0159986 A1 | 7/2005 | Breeland et al. |
| 2005/0177075 A1 | 8/2005 | Meunier et al. |
| 2005/0182462 A1 | 8/2005 | Chornenky et al. |
| 2005/0187495 A1 | 8/2005 | Quistgaard et al. |
| 2005/0187597 A1 | 8/2005 | Vanderschuit |
| 2005/0203446 A1 | 9/2005 | Takashima |
| 2005/0215987 A1 | 9/2005 | Slatkine |
| 2005/0222565 A1 | 10/2005 | Manstein |
| 2005/0251117 A1 | 11/2005 | Anderson et al. |
| 2005/0251120 A1 | 11/2005 | Anderson et al. |
| 2005/0261753 A1 | 11/2005 | Littrup et al. |
| 2005/0277859 A1 | 12/2005 | Carlsmith et al. |
| 2005/0283144 A1 | 12/2005 | Shiono et al. |
| 2006/0030778 A1 | 2/2006 | Mendlein et al. |
| 2006/0035380 A1 | 2/2006 | Saint-Leger |
| 2006/0036300 A1 | 2/2006 | Kreindel |
| 2006/0041704 A1 | 2/2006 | Choi |
| 2006/0074313 A1* | 4/2006 | Slayton ............... A61B 8/14 600/439 |
| 2006/0079852 A1 | 4/2006 | Bubb et al. |
| 2006/0094988 A1 | 5/2006 | Tosaya et al. |
| 2006/0106836 A1 | 5/2006 | Masugi et al. |
| 2006/0111613 A1 | 5/2006 | Boutillette et al. |
| 2006/0122509 A1 | 6/2006 | Desilets |
| 2006/0189964 A1 | 8/2006 | Anderson et al. |
| 2006/0195168 A1 | 8/2006 | Dunbar et al. |
| 2006/0200063 A1 | 9/2006 | Munro et al. |
| 2006/0206040 A1 | 9/2006 | Greenberg et al. |
| 2006/0206110 A1 | 9/2006 | Knowlton et al. |
| 2006/0234899 A1 | 10/2006 | Nekmard et al. |
| 2006/0259102 A1 | 11/2006 | Slatkine |
| 2006/0265032 A1 | 11/2006 | Hennings et al. |
| 2006/0270745 A1 | 11/2006 | Hunt et al. |
| 2006/0293734 A1 | 12/2006 | Scott et al. |
| 2007/0010811 A1 | 1/2007 | Stern et al. |
| 2007/0010861 A1 | 1/2007 | Anderson et al. |
| 2007/0032561 A1 | 2/2007 | Lin et al. |
| 2007/0038156 A1 | 2/2007 | Rosenberg |
| 2007/0055156 A1 | 3/2007 | Desilets et al. |
| 2007/0055173 A1 | 3/2007 | DeLonzor et al. |
| 2007/0055179 A1 | 3/2007 | Deem et al. |
| 2007/0055180 A1 | 3/2007 | Deem et al. |
| 2007/0055181 A1 | 3/2007 | Deem et al. |
| 2007/0073367 A1 | 3/2007 | Jones et al. |
| 2007/0078502 A1 | 4/2007 | Weber et al. |
| 2007/0100398 A1 | 5/2007 | Sloan |
| 2007/0106342 A1 | 5/2007 | Schumann |
| 2007/0129714 A1 | 6/2007 | Elkins et al. |
| 2007/0135876 A1 | 6/2007 | Weber |
| 2007/0141265 A1 | 6/2007 | Thomson |
| 2007/0179482 A1 | 8/2007 | Anderson |
| 2007/0198071 A1 | 8/2007 | Ting et al. |
| 2007/0219540 A1 | 9/2007 | Masotti et al. |
| 2007/0233226 A1* | 10/2007 | Kochamba ............ A61B 17/02 623/1.12 |
| 2007/0239075 A1 | 10/2007 | Rosenberg et al. |
| 2007/0239150 A1 | 10/2007 | Zvuloni et al. |
| 2007/0249519 A1 | 10/2007 | Guha et al. |
| 2007/0255187 A1 | 11/2007 | Branch |
| 2007/0255274 A1 | 11/2007 | Stern et al. |
| 2007/0255362 A1* | 11/2007 | Levinson ................ A61F 7/10 607/96 |
| 2007/0265585 A1 | 11/2007 | Joshi et al. |
| 2007/0265614 A1 | 11/2007 | Stern et al. |
| 2007/0270925 A1 | 11/2007 | Levinson |
| 2007/0282249 A1 | 12/2007 | Quisenberry et al. |
| 2007/0282318 A1 | 12/2007 | Spooner et al. |
| 2008/0014627 A1 | 1/2008 | Merchant et al. |
| 2008/0046047 A1 | 2/2008 | Jacobs |
| 2008/0058784 A1 | 3/2008 | Manstein et al. |
| 2008/0077201 A1 | 3/2008 | Levinson et al. |
| 2008/0077202 A1 | 3/2008 | Levinson |
| 2008/0077211 A1* | 3/2008 | Levinson ................ A61F 7/10 607/108 |
| 2008/0097207 A1 | 4/2008 | Cai et al. |
| 2008/0139901 A1 | 6/2008 | Altshuler et al. |
| 2008/0140061 A1 | 6/2008 | Toubia et al. |
| 2008/0140371 A1 | 6/2008 | Warner |
| 2008/0161892 A1 | 7/2008 | Mercuro et al. |
| 2008/0183164 A1* | 7/2008 | Elkins ................... A61B 18/02 606/21 |
| 2008/0188915 A1 | 8/2008 | Mills et al. |
| 2008/0248554 A1 | 10/2008 | Merchant et al. |
| 2008/0269851 A1 | 10/2008 | Deem et al. |
| 2008/0287839 A1 | 11/2008 | Rosen et al. |
| 2008/0300529 A1 | 12/2008 | Reinstein |
| 2008/0312651 A1 | 12/2008 | Pope et al. |
| 2009/0012434 A1 | 1/2009 | Anderson |
| 2009/0018623 A1 | 1/2009 | Levinson et al. |
| 2009/0018624 A1 | 1/2009 | Levinson et al. |
| 2009/0018625 A1 | 1/2009 | Levinson et al. |
| 2009/0018626 A1 | 1/2009 | Levinson et al. |
| 2009/0018627 A1 | 1/2009 | Levinson et al. |
| 2009/0024023 A1 | 1/2009 | Welches et al. |
| 2009/0076488 A1 | 3/2009 | Welches et al. |
| 2009/0112134 A1 | 4/2009 | Avni |
| 2009/0118722 A1 | 5/2009 | Ebbers et al. |
| 2009/0149929 A1 | 6/2009 | Levinson et al. |
| 2009/0149930 A1 | 6/2009 | Schenck |
| 2009/0171253 A1 | 7/2009 | Davenport |
| 2009/0171334 A1 | 7/2009 | Elkins et al. |
| 2009/0221938 A1 | 9/2009 | Rosenberg et al. |
| 2009/0226424 A1 | 9/2009 | Hsu |
| 2009/0276018 A1 | 11/2009 | Brader |
| 2009/0281464 A1 | 11/2009 | Cioanta et al. |
| 2009/0299234 A1 | 12/2009 | Cho et al. |
| 2009/0306749 A1 | 12/2009 | Mulindwa |
| 2009/0312676 A1 | 12/2009 | Rousso et al. |
| 2009/0312693 A1 | 12/2009 | Thapliyal et al. |
| 2009/0326621 A1 | 12/2009 | El-Galley |
| 2010/0015190 A1 | 1/2010 | Hassler |
| 2010/0028969 A1 | 2/2010 | Mueller et al. |
| 2010/0030306 A1 | 2/2010 | Edelman et al. |
| 2010/0036295 A1 | 2/2010 | Altshuler et al. |
| 2010/0042087 A1 | 2/2010 | Goldboss et al. |
| 2010/0049178 A1 | 2/2010 | Deem et al. |
| 2010/0081971 A1 | 4/2010 | Allison |
| 2010/0087806 A1 | 4/2010 | Da Silva et al. |
| 2010/0152824 A1 | 6/2010 | Allison |
| 2010/0168726 A1 | 7/2010 | Brookman |

(56) References Cited

U.S. PATENT DOCUMENTS

| | | |
|---|---|---|
| 2010/0179531 A1 | 7/2010 | Nebrigic et al. |
| 2010/0198064 A1 | 8/2010 | Perl et al. |
| 2010/0217349 A1 | 8/2010 | Fahey et al. |
| 2010/0241023 A1 | 9/2010 | Gilbert |
| 2010/0268220 A1 | 10/2010 | Johnson et al. |
| 2010/0280582 A1 | 11/2010 | Baker et al. |
| 2011/0009860 A1 | 1/2011 | Chornenky et al. |
| 2011/0040235 A1 | 2/2011 | Castel |
| 2011/0040299 A1 | 2/2011 | Kim et al. |
| 2011/0046523 A1 | 2/2011 | Altshuler et al. |
| 2011/0060323 A1 | 3/2011 | Baust et al. |
| 2011/0066083 A1 | 3/2011 | Tosaya et al. |
| 2011/0066216 A1 | 3/2011 | Ting et al. |
| 2011/0077557 A1 | 3/2011 | Wing et al. |
| 2011/0077723 A1 | 3/2011 | Parish et al. |
| 2011/0112405 A1 | 5/2011 | Barthe et al. |
| 2011/0112520 A1 | 5/2011 | Kreindel |
| 2011/0144631 A1 | 6/2011 | Elkins et al. |
| 2011/0152849 A1 | 6/2011 | Baust et al. |
| 2011/0172651 A1 | 7/2011 | Altshuler et al. |
| 2011/0189129 A1 | 8/2011 | Qiu et al. |
| 2011/0196395 A1 | 8/2011 | Maschke |
| 2011/0196438 A1 | 8/2011 | Mnozil et al. |
| 2011/0202048 A1 | 8/2011 | Nebrigic et al. |
| 2011/0238050 A1 | 9/2011 | Allison et al. |
| 2011/0238051 A1 | 9/2011 | Levinson et al. |
| 2011/0257642 A1 | 10/2011 | Griggs, III |
| 2011/0288537 A1 | 11/2011 | Halaka |
| 2011/0300079 A1 | 12/2011 | Martens et al. |
| 2011/0301585 A1 | 12/2011 | Goulko |
| 2011/0313411 A1* | 12/2011 | Anderson ............... A61F 7/00 606/25 |
| 2011/0313412 A1 | 12/2011 | Kim et al. |
| 2012/0010609 A1 | 1/2012 | Deem et al. |
| 2012/0016239 A1 | 1/2012 | Barthe et al. |
| 2012/0022518 A1 | 1/2012 | Levinson |
| 2012/0022622 A1 | 1/2012 | Johnson et al. |
| 2012/0035475 A1 | 2/2012 | Barthe et al. |
| 2012/0035476 A1 | 2/2012 | Barthe et al. |
| 2012/0041525 A1 | 2/2012 | Karni |
| 2012/0046547 A1 | 2/2012 | Barthe et al. |
| 2012/0053458 A1 | 3/2012 | Barthe et al. |
| 2012/0065629 A1 | 3/2012 | Elkins et al. |
| 2012/0083862 A1 | 4/2012 | Altshuler et al. |
| 2012/0089211 A1* | 4/2012 | Curtis ................. A61B 18/02 607/105 |
| 2012/0101549 A1 | 4/2012 | Schumann |
| 2012/0109041 A1 | 5/2012 | Munz |
| 2012/0158100 A1 | 6/2012 | Schomacker |
| 2012/0209363 A1 | 8/2012 | Williams, III et al. |
| 2012/0233736 A1 | 9/2012 | Tepper et al. |
| 2012/0239123 A1 | 9/2012 | Weber et al. |
| 2012/0253416 A1 | 10/2012 | Erez et al. |
| 2012/0259322 A1 | 10/2012 | Fourkas et al. |
| 2012/0277674 A1 | 11/2012 | Clark, III et al. |
| 2012/0310232 A1 | 12/2012 | Erez |
| 2013/0018236 A1 | 1/2013 | Altshuler et al. |
| 2013/0019374 A1 | 1/2013 | Schwartz |
| 2013/0035680 A1 | 2/2013 | Ben-Haim et al. |
| 2013/0066309 A1 | 3/2013 | Levinson |
| 2013/0073017 A1 | 3/2013 | Liu et al. |
| 2013/0079684 A1 | 3/2013 | Rosen et al. |
| 2013/0116758 A1 | 5/2013 | Levinson et al. |
| 2013/0116759 A1 | 5/2013 | Levinson et al. |
| 2013/0150844 A1 | 6/2013 | Deem et al. |
| 2013/0158440 A1 | 6/2013 | Allison |
| 2013/0158636 A1 | 6/2013 | Ting et al. |
| 2013/0166003 A1 | 6/2013 | Johnson et al. |
| 2013/0190744 A1 | 7/2013 | Avram et al. |
| 2013/0238062 A1 | 9/2013 | Ron et al. |
| 2013/0245507 A1 | 9/2013 | Khorassani |
| 2013/0253384 A1 | 9/2013 | Anderson et al. |
| 2013/0253493 A1 | 9/2013 | Anderson et al. |
| 2013/0253494 A1 | 9/2013 | Anderson et al. |
| 2013/0253495 A1 | 9/2013 | Anderson et al. |
| 2013/0253496 A1 | 9/2013 | Anderson et al. |
| 2013/0303904 A1 | 11/2013 | Barthe et al. |
| 2013/0303905 A1 | 11/2013 | Barthe et al. |
| 2013/0331914 A1 | 12/2013 | Lee et al. |
| 2014/0005759 A1 | 1/2014 | Fahey et al. |
| 2014/0005760 A1 | 1/2014 | Levinson et al. |
| 2014/0067025 A1 | 3/2014 | Levinson et al. |
| 2014/0142469 A1 | 5/2014 | Britva et al. |
| 2014/0200487 A1 | 7/2014 | Ramdas et al. |
| 2014/0200488 A1 | 7/2014 | Seo et al. |
| 2014/0222121 A1 | 8/2014 | Spence et al. |
| 2014/0277219 A1 | 9/2014 | Nanda |
| 2014/0277302 A1 | 9/2014 | Weber et al. |
| 2014/0277303 A1 | 9/2014 | Biser et al. |
| 2014/0303697 A1* | 10/2014 | Anderson ............. A61F 7/0085 607/104 |
| 2015/0209174 A1 | 7/2015 | Abreu |
| 2015/0216719 A1* | 8/2015 | DeBenedictis ......... A61F 7/007 601/2 |
| 2015/0216720 A1 | 8/2015 | DeBenedictis et al. |
| 2015/0216816 A1 | 8/2015 | O'Neil et al. |
| 2015/0223975 A1* | 8/2015 | Anderson ............. A61B 18/02 607/104 |
| 2015/0283022 A1 | 10/2015 | Lee et al. |
| 2015/0328077 A1 | 11/2015 | Levinson |
| 2015/0335468 A1 | 11/2015 | Rose et al. |
| 2015/0342780 A1 | 12/2015 | Levinson et al. |
| 2016/0051308 A1 | 2/2016 | Pennybacker et al. |
| 2016/0051401 A1 | 2/2016 | Yee et al. |
| 2016/0135985 A1 | 5/2016 | Anderson |
| 2016/0296269 A1* | 10/2016 | Rubinsky ................ C25B 1/26 |
| 2016/0324684 A1 | 11/2016 | Levinson et al. |
| 2017/0007309 A1 | 1/2017 | DeBenedictis et al. |
| 2017/0079833 A1 | 3/2017 | Frangineas, Jr. et al. |
| 2017/0165105 A1* | 6/2017 | Anderson ............. A61N 5/0616 |
| 2017/0196731 A1 | 7/2017 | DeBenedictis et al. |
| 2017/0224528 A1* | 8/2017 | Berg .................... A61F 7/0053 |
| 2017/0239079 A1 | 8/2017 | Root et al. |
| 2017/0325992 A1 | 11/2017 | DeBenedictis et al. |
| 2017/0325993 A1 | 11/2017 | Jimenez Lozano et al. |
| 2017/0326042 A1 | 11/2017 | Ze et al. |
| 2017/0326346 A1 | 11/2017 | Jimenez et al. |
| 2018/0185081 A1 | 7/2018 | O'Neil et al. |
| 2018/0185189 A1 | 7/2018 | Weber et al. |
| 2018/0263677 A1 | 9/2018 | Hilton et al. |
| 2018/0271767 A1 | 9/2018 | Jimenez Lozano et al. |
| 2018/0310950 A1 | 11/2018 | Yee et al. |
| 2019/0125424 A1 | 5/2019 | Debenedictis et al. |
| 2019/0142493 A1 | 5/2019 | Debenedictis et al. |

FOREIGN PATENT DOCUMENTS

| | | |
|---|---|---|
| CA | 2585214 A1 | 10/2007 |
| CH | 333982 A | 11/1958 |
| CN | 86200604 U | 10/1987 |
| CN | 2514795 Y | 10/2002 |
| CN | 2514811 Y | 10/2002 |
| CN | 1511503 A | 7/2004 |
| CN | 1741777 A | 3/2006 |
| CN | 1817990 A | 8/2006 |
| CN | 2843367 Y | 12/2006 |
| CN | 2850584 Y | 12/2006 |
| CN | 2850585 Y | 12/2006 |
| CN | 200970265 Y | 11/2007 |
| CN | 101259329 A | 9/2008 |
| CN | 101309657 A | 11/2008 |
| DE | 532976 C | 9/1931 |
| DE | 2851602 A1 | 6/1980 |
| DE | 4213584 A1 | 11/1992 |
| DE | 4224595 A1 | 1/1994 |
| DE | 4238291 A1 | 5/1994 |
| DE | 4445627 A1 | 6/1996 |
| DE | 19800416 A1 | 7/1999 |
| EP | 263069 A2 | 4/1988 |
| EP | 0397043 A1 | 11/1990 |
| EP | 0406244 A1 | 1/1991 |
| EP | 560309 A1 | 9/1993 |
| EP | 0598824 A1 | 6/1994 |
| EP | 1030611 A1 | 8/2000 |

(56) References Cited

FOREIGN PATENT DOCUMENTS

| | | |
|---|---|---|
| EP | 1201266 A1 | 5/2002 |
| EP | 1568395 A1 | 8/2005 |
| EP | 2260801 A2 | 12/2010 |
| EP | 2289598 A1 | 3/2011 |
| EP | 2527005 A1 | 11/2012 |
| FR | 854937 A | 4/1940 |
| FR | 2744358 A1 | 8/1997 |
| FR | 2745935 A1 | 9/1997 |
| FR | 2767476 A1 | 2/1999 |
| FR | 2776920 A1 | 10/1999 |
| FR | 2789893 A1 | 8/2000 |
| FR | 2805989 A1 | 9/2001 |
| GB | 387960 A | 2/1933 |
| GB | 2120944 A | 12/1983 |
| GB | 2202447 A | 9/1988 |
| GB | 2248183 A | 4/1992 |
| GB | 2263872 A | 8/1993 |
| GB | 2286660 A | 8/1995 |
| GB | 2323659 A | 9/1998 |
| JP | 58187454 A | 11/1983 |
| JP | S6094113 U | 6/1985 |
| JP | 62082977 A | 4/1987 |
| JP | 63076895 A | 4/1988 |
| JP | 01223961 A | 9/1989 |
| JP | 03051964 A | 3/1991 |
| JP | 03259975 A | 11/1991 |
| JP | 04093597 A | 3/1992 |
| JP | 06261933 A | 9/1994 |
| JP | 07194666 A | 8/1995 |
| JP | 07268274 A | 10/1995 |
| JP | 09164163 A | 6/1997 |
| JP | 10216169 A | 8/1998 |
| JP | 10223961 A | 8/1998 |
| JP | 2000503154 A | 3/2000 |
| JP | 3065657 B2 | 7/2000 |
| JP | 2001046416 A | 2/2001 |
| JP | 2002125993 A | 5/2002 |
| JP | 2002224051 A | 8/2002 |
| JP | 2002282295 A | 10/2002 |
| JP | 2002290397 A | 10/2002 |
| JP | 2002543668 A | 12/2002 |
| JP | 2003190201 A | 7/2003 |
| JP | 2004013600 A | 1/2004 |
| JP | 2004073812 A | 3/2004 |
| JP | 2004159666 A | 6/2004 |
| JP | 2005039790 A | 2/2005 |
| JP | 2005065984 A | 3/2005 |
| JP | 2005110755 A | 4/2005 |
| JP | 2005509977 A | 4/2005 |
| JP | 3655820 B2 | 6/2005 |
| JP | 2005520608 A | 7/2005 |
| JP | 2005237908 A | 9/2005 |
| JP | 2005323716 A | 11/2005 |
| JP | 2006026001 A | 2/2006 |
| JP | 2006130055 A | 5/2006 |
| JP | 2006520949 A | 9/2006 |
| JP | 2007270459 A | 10/2007 |
| JP | 2008532591 A | 8/2008 |
| JP | 2009515232 A | 4/2009 |
| JP | 2009189757 A | 8/2009 |
| KR | 200173222 Y1 | 12/1999 |
| KR | 1020040094508 A | 11/2004 |
| KR | 20090000258 U | 1/2009 |
| KR | 1020130043299 A | 4/2013 |
| KR | 1020140038165 A | 3/2014 |
| RU | 2036667 C1 | 6/1995 |
| SU | 532976 A1 | 11/1978 |
| TW | 0476644 B | 2/2002 |
| WO | 8503216 A1 | 8/1985 |
| WO | 9114417 A1 | 10/1991 |
| WO | 9300807 A1 | 1/1993 |
| WO | 9404116 A1 | 3/1994 |
| WO | 9623447 A1 | 8/1996 |
| WO | 9626693 A1 | 9/1996 |
| WO | 9636293 A1 | 11/1996 |
| WO | 9637158 A1 | 11/1996 |
| WO | 9704832 A1 | 2/1997 |
| WO | 9705828 A1 | 2/1997 |
| WO | 9722262 A2 | 6/1997 |
| WO | 9724088 A1 | 7/1997 |
| WO | 9725798 A1 | 7/1997 |
| WO | 9748440 A1 | 12/1997 |
| WO | 9829134 A2 | 7/1998 |
| WO | 9831321 A1 | 7/1998 |
| WO | 9841156 A1 | 9/1998 |
| WO | 9841157 A1 | 9/1998 |
| WO | 9909928 A1 | 3/1999 |
| WO | 9916502 A1 | 4/1999 |
| WO | 9938469 A1 | 8/1999 |
| WO | 9949937 A1 | 10/1999 |
| WO | 0044346 A1 | 8/2000 |
| WO | 0044349 A1 | 8/2000 |
| WO | 0065770 A1 | 11/2000 |
| WO | 0067685 A1 | 11/2000 |
| WO | 0100269 A1 | 1/2001 |
| WO | 0113989 A1 | 3/2001 |
| WO | 0114012 A1 | 3/2001 |
| WO | 0134048 A1 | 5/2001 |
| WO | 0205736 A1 | 1/2002 |
| WO | 02102921 A1 | 12/2002 |
| WO | 03007859 A1 | 1/2003 |
| WO | 03078596 A2 | 9/2003 |
| WO | 03079916 A1 | 10/2003 |
| WO | 2004000098 A2 | 12/2003 |
| WO | 2004080279 A2 | 9/2004 |
| WO | 2004090939 A2 | 10/2004 |
| WO | 2005033957 A1 | 4/2005 |
| WO | 2005046540 A1 | 5/2005 |
| WO | 2005060354 A2 | 7/2005 |
| WO | 2005096979 A1 | 10/2005 |
| WO | 2005112815 A1 | 12/2005 |
| WO | 2006066226 A1 | 6/2006 |
| WO | 2006094348 A1 | 9/2006 |
| WO | 2006106836 A1 | 10/2006 |
| WO | 2006116603 A2 | 11/2006 |
| WO | 2006127467 A2 | 11/2006 |
| WO | 2007012083 A2 | 1/2007 |
| WO | 2007028975 A1 | 3/2007 |
| WO | 2007041642 A2 | 4/2007 |
| WO | 2007101039 A1 | 9/2007 |
| WO | 2007127924 A2 | 11/2007 |
| WO | 2007145421 A1 | 12/2007 |
| WO | 2007145422 A1 | 12/2007 |
| WO | 2008006018 A2 | 1/2008 |
| WO | 2008039556 A1 | 4/2008 |
| WO | 2008039557 A1 | 4/2008 |
| WO | 2008055243 A2 | 5/2008 |
| WO | 2008143678 A1 | 11/2008 |
| WO | 2009011708 A1 | 1/2009 |
| WO | 2009026471 A1 | 2/2009 |
| WO | 2010077841 A1 | 7/2010 |
| WO | 2010127315 A2 | 11/2010 |
| WO | 2012012296 A1 | 1/2012 |
| WO | 2012103242 A1 | 8/2012 |
| WO | 2013013059 A1 | 1/2013 |
| WO | 2013075006 A1 | 5/2013 |
| WO | 2013075016 A1 | 5/2013 |
| WO | 2013190337 A1 | 12/2013 |
| WO | 2014151872 A3 | 9/2014 |
| WO | 2014191263 A1 | 12/2014 |
| WO | 2015117001 A1 | 8/2015 |
| WO | 2015117005 A1 | 8/2015 |
| WO | 2015117026 A2 | 8/2015 |
| WO | 2015117032 A1 | 8/2015 |
| WO | 2015117036 A2 | 8/2015 |
| WO | 2016028796 A1 | 2/2016 |
| WO | 2016048721 A1 | 3/2016 |

OTHER PUBLICATIONS

Al-Sakere, B. et al. "Tumor Ablation with Irreversible Electroporation," PLoS One, Issue 11, Nov. 2007, 8 pages.

(56) References Cited

OTHER PUBLICATIONS

Alster, T. et al., "Cellulite Treatment Using a Novel Combination Radiofrequency, Infrared Light, and Mechanical Tissue Manipulation Device," Journal of Cosmetic and Laser Therapy, vol. 7, 2005, pp. 81-85.
Ardevol, A. et al., "Cooling Rates of Tissue Samples During Freezing with Liquid Nitrogen," Journal of Biochemical and Biophysical Methods, vol. 27, 1993, pp. 77-86.
Arena, C. B. et al., "High-Frequency Irreversible Electroporation (H-FIRE) for Non-Thermal Ablation Without Muscle Contraction," BioMedical Engineering OnLine 2011, 10:102, Nov. 21, 2011, 21 pgs.
Becker, S. M. et al. "Local Temperature Rises Influence In Vivo Electroporation Pore Development: A Numerical Stratum Corneum Lipid Phase Transition Model," Journal of Biomechanical Engineering, vol. 129, Oct. 2007, pp. 712-721.
Bohm, T. et al., "Saline-Enhanced Radiofrequency Ablation of Breast Tissue: an in Vitro Feasibility Study," Investigative Radiology, vol. 35 (3), 2000, pp. 149-157.
Bondei, E. et al., "Disorders of Subcutaneous Tissue (Cold Panniculitis)," Dermatology in General Medicine, Fourth Edition, vol. 1, Chapter 108, 1993, Section 16, pp. 1333-1334.
Burge, S.M. et al., "Hair Follicle Destruction and Regeneration in Guinea Pig Skin after Cutaneous Freeze Injury," Cryobiology, 27(2), 1990, pp. 153-163.
Coban, Y. K. et al., "Ischemia-Reperfusion Injury of Adipofascial Tissue: An Experimental Study Evaluating Early Histologic and Biochemical Alterations in Rats," Mediators of Inflammation, 2005, 5, pp. 304-308.
Del Pino, M. E. et al. "Effect of Controlled Volumetric Tissue Heating with Radiofrequency on Cellulite and the Subcutaneous Tissue of the Buttocks and Thighs," Journal of Drugs in Dermatology, vol. 5, Issue 8, Sep. 2006, pp. 714-722.
Donski, P. K. et al., "The Effects of Cooling no Experimental Free Flap Survival," British Journal of Plastic Surgery, vol. 33, 1980, pp. 353-360.
Duck, F. A., Physical Properties of Tissue, Academic Press Ltd., chapters 4 & 5, 1990, pp. 73-165.
Duncan, W. C. et al., "Cold Panniculitis," Archives of Dermatology, vol. 94, Issue 6, Dec. 1966, pp. 722-724.
Epstein, E. H. et al., "Popsicle Panniculitis," The New England Journal of Medicine, 282(17), Apr. 23, 1970, pp. 966-967.
Fournier, L. et al. "Lattice Model for the Kinetics of Rupture of Fluid Bilayer Membranes," Physical Review, vol. 67, 2003, pp. 051908-1-051908-11.
Gabriel, S. et al., "The Dielectric Properties of Biological Tissues: II. Measurements in the Frequency Range 10 Hz to 20 GHz," Physics in Medicine and Biology, vol. 41, 1996, pp. 2251-2269.
Gage, A. "Current Progress in Cryosurgery," Cryobiology 25, 1988, pp. 483-486.
Gatto, H. "Effects of Thermal Shocks on Interleukin-1 Levels and Heat Shock Protein 72 (HSP72) Expression in Normal Human Keratinocytes," PubMed, Archives of Dermatological Research, vol. 284, Issue 7, 1992: pp. 414-417 [Abstract].
Hale, H. B. et al., "Influence of Chronic Heat Exposure and Prolonged Food Deprivation on Excretion of Magnesium, Phosphorus, Calcium, Hydrogen Ion & Ketones," Aerospace Medicine, vol. 39—No. 9, Sep. 1968, pp. 919-926.
Heller Page, E. et al., "Temperature-dependent skin disorders," Journal of the American Academy of Dermatology, vol. 18, No. 5, Pt 1, May 1988, pp. 1003-1019.
Hemmingsson, A. et al. "Attenuation in Human Muscle and Fat Tissue in Vivo and in Vitro," Acra Radiologica Diagnosis, vol. 23, No. 2, 1982, pp. 149-151.
Henry, F. et al., "Les Dermatoses Hivernales," Rev Med Liege, 54:11, 1999, pp. 864-866. [Abstract Attached].
Hernan, P. et al., "Study for the evaluation of the efficacy of Lipocryolysis (EEEL)", Nov. 30, 2011.
Hernan, R. P., "A Study to Evaluate the Action of Lipocryolysis", 33(3) CryoLellers, 2012, pp. 176-180.
Holland, DB. et al. "Cold shock induces the synthesis of stress proteins in human keratinocytes," PubMed Journal of Investigative Dermatology; 101(2): Aug. 1993, pp. 196-199.
Holman, W. L. et al., "Variation in Cryolesion Penetration Due to Probe Size and Tissue Thermal Conductivity," The Annals of Thoracic Surgery, vol. 53, 1992, pp. 123-126.
Hong, J.S. et al., "Patterns of Ice Formation in Normal and Malignant Breast Tissue," Cryobiology 31, 1994, pp. 109-120.
Huang et al. "Comparative Proteomic Profiling of Murine Skin," Journal of Investigative Dermatology, vol. 121(1), Jul. 2003, pp. 51-64.
Isambert, H. "Understanding the Electroporation of Cells and Artificial Bilayer Membranes," Physical Review Letters, vol. 80, No. 15, 1998, pp. 3404-3707.
Jalian, H. R. et al., "Cryolipolysis: A Historical Perspective and Current Clinical Practice", 32(1) Semin. Cutan. Med. Surg., 2013, pp. 31-34.
Kellum, R. E. et al., "Sclerema Neonatorum: Report of Case and Analysis of Subcutaneous and Epidermal-Dermal Lipids by Chromatographic Methods," Archives of Dermatology, vol. 97, Apr. 1968, pp. 372-380.
Koska, J. et al., "Endocrine Regulation of Subcutaneous Fat Metabolism During Cold Exposure in Humans," Annals of the New York Academy of Sciences, vol. 967, 2002,pp. 500-505.
Kundu, S. K. et al., "Breath Acetone Analyzer: Diagnostic Tool to Monitor Dietary Fat Loss," Clinical Chemistry, vol. 39, Issue (1), 1993, pp. 87-92.
Kundu, S. K. et al., "Novel Solid-Phase Assay of Ketone Bodies in Urine," Clinical Chemistry, vol. 37, Issue (9), 1991, pp. 1565-1569.
Kuroda, S. et al. "Thermal Distribution of Radio-Frequency Inductive Hyperthermia Using an Inductive Aperture-Type Applicator: Evaluation of the Effect of Tumor Size and Depth", Medical and Biological Engineering and Computing, vol. 37, 1999, pp. 285-290.
Laugier, P. et al., "In Vivo Results with a New Device for Ultrasonic Monitoring of Pig Skin Cryosurgery: The Echographic Cryprobe," The Society for Investigative Dermatology, Inc., vol. 111, No. 2, Aug. 1998, pp. 314-319.
Levchenko et al., "Effect of Dehydration on Lipid Metabolism" Ukrainskii Biokhimicheskii Zhurnal, vol. 50, Issue 1, 1978, pp. 95-97.
Lidagoster, MD et al., "Comparison of Autologous Fat Transfer in Fresh, Refrigerated, and Frozen Specimens: An Animal Model," Annals of Plastic Surgery, vol. 44, No. 5, May 2000, pp. 512-515.
Liu, A. Y.-C. et al., "Transient Cold Shock Induces the Heat Shock Response upon Recovery at 37 C in Human Cells," Journal of Biological Chemistry, , 269(20), May 20, 1994, pp. 14768-14775.
L'Vova, S.P. "Lipid Levels and Lipid Peroxidation in Frog Tissues During Hypothermia and Hibernation" Ukrainskii Biokhimicheskii Zhurnal, vol. 62, Issue 1, 1990, pp. 65-70.
Maize, J.C. "Panniculitis," Cutaneous Pathology, Chapter 13, 1998, 327-344.
Malcolm, G. T. et al., "Fatty Acid Composition of Adipose Tissue in Humans: Differences between Subcutaneous Sites," The American Journal of Clinical Nutrition, vol. 50, 1989, pp. 288-291.
Manstein, D. et al. "A Novel Cryotherapy Method of Non-invasive, Selective Lipolysis," LasersSurg.Med 40:S20, 2008, p. 104.
Manstein, D. et al. "Selective Cryolysis: A Novel Method of Non-Invasive Fat Removal," Lasers in Surgery and Medicine: The Official Journal of the ASLMS, vol. 40, No. 9, Nov. 2008, pp. 595-604.
Mayoral, "Case Reports: Skin Tightening with a Combined Unipolar and Bipolar Radiofrequency Device," Journal of Drugs in Dermatology, 2007, pp. 212-215.
Mazur, P. "Cryobiology: the Freezing of Biological Systems," Science, 68, 1970, pp. 939-949.
Merrill, T. "A Chill to the Heart: A System to Deliver Local Hypothermia Could One Day Improve the Lives of Heart-Attack Patients," Mechanical Engineering Magazine, Oct. 2010, 10 pages.
Miklavcic, D. et al. "Electroporation-Based Technologies and Treatments," The Journal of Membrane Biology (2010) 236:1-2, 2 pgs.
Moschella, S. L. et al., "Diseases of the Subcutaneous Tissue," in Dermatology, Second Edition, vol. 2, 1985 Chapter 19, Section II (W.B. Saunders Company, 1980) pp. 1169-1181.

(56) References Cited

OTHER PUBLICATIONS

Murphy, J. V. et al., "Frostbite: Pathogenesis and Treatment" The Journal of Trauma: Injury, Infection, and Critical Care, vol. 48, No. 1, Jan. 2000, pp. 171-178.
Nagao, T. et al., "Dietary Diacylglycerol Suppresses Accumulation of Body Fat Compared to Triacylglycerol in Men a Double-Blind Controlled Trial," The Journal of Nutrition, vol. 130, Issue (4), 2000, pp. 792-797.
Nagle, W. A. et al. "Cultured Chinese Hamster Cells Undergo Apoptosis After Exposure to Cold but Nonfreezing Temperatures," Cryobiology 27, 1990, pp. 439-451.
Nagore, E. et al., "Lipoatrophia Semicircularis—a Traumatic Panniculitis: Report of Seven Cases and Review of the Literature," Journal of the American Academy of Dermatology, vol. 39, Nov. 1998, pp. 879-881.
Nanda, G.S. et al., "Studies on electroporation of thermally and chemically treated human erythrocytes," Bioelectrochemistry and Bioenergetics, 34, 1994, pp. 129-134, 6 pgs.
Narins, D.J. et al. "Non-Surgical Radiofrequency Facelift", The Journal of Drugs in Dermatology, vol. 2, Issue 5, 2003, pp. 495-500.
Nielsen, B. "Thermoregulation in Rest and Exercise," Acta Physiologica Scandinavica Supplementum, vol. 323 (Copenhagen 1969), pp. 7-74.
Nishikawa, H. et al. "Ultrastructural Changes and Lipid Peroxidation in Rat Adipomusculocutaneous Flap Isotransplants after Normothermic Storage and Reperfusion," Transplantation, vol. 54, No. 5, 1992, pp. 795-801.
Nurnberger, F. "So-Called Cellulite: An Invented Disease," Journal of Dermatologic Surgery and Oncology, Mar. 1978, pp. 221-229.
Pease, G. R. et al., "An Integrated Probe for Magnetic Resonance Imaging Monitored Skin Cryosurgery," Journal of Biomedical Engineering, vol. 117, Feb. 1995, pp. 59-63.
Pech, P. et al., "Attenuation Values, Volume Changes and Artifacts in Tissue Due to Freezing," Acta Radiologica, vol. 28, Issue 6, 1987, pp. 779-782.
Peterson, L. J. et al., "Bilateral Fat Necrosis of the Scrotum," Journal of Urology, vol. 116, 1976, pp. 825-826.
Phinney, S. D. et al., "Human Subcutaneous Adipose Tissue Shows Site-Specific Differences in Fatty Acid Composition," The American Journal of Clinical Nutrition, vol. 60, 1994, pp. 725-729.
Pierard, G.E. et al., "Cellulite: From Standing Fat Herniation to Hypodermal Stretch Marks," The American Journal of Dermatology, vol. 22, Issue 1, 2000, pp. 34-37, [Abstract].
Pope, K. et al. "Selective Fibrous Septae Heating: An Additional Mechanism of Action for Capacitively Coupled Monopolar Radiofrequency" Thermage, Inc. Article, Feb. 2005, 6pgs.
Quinn, P. J. "A Lipid-Phase Separation Model of Low-Temperature Damage to Biological Membranes," Cryobiology, 22, 1985, 128-146.
Rabi, T. et al., "Metabolic Adaptations in Brown Adipose Tissue of the Hamster in Extreme Ambient Temperatures," American Journal of Physiology, vol. 231, Issue 1, Jul. 1976, pp. 153-160.
Renold, A.E. et al. "Adipose Tissue" in Handbook of Physiology, Chapter 15, (Washington, D.C., 1965) pp. 169-176.
Rossi, A. B. R. et al. "Cellulite: a Review," European Academy of Dermatology and Venercology, 2000, pp. 251-262, 12 pgs.
Rubinsky, B. "Principles of Low Temperature Cell Preservation," Heart Failure Reviews, vol. 8, 2003, pp. 277-284.
Rubinsky, B. et al., "Cryosurgery: Advances in the Application of low Temperatures to Medicine," International Journal of Refrigeration, vol. 14, Jul. 1991, pp. 190-199.
Saleh, K.Y. et al., "Two-Dimensional Ultrasound Phased Array Design for Tissue Ablation for Treatment of Benign Prostatic Hyperplasia," International Journal of Hyperthermia, vol. 20, No. 1, Feb. 2004, pp. 7-31.
Schoning, P. et al., "Experimental Frostbite: Freezing Times, Rewarming Times, and Lowest Temperatures of Pig Skin Exposed to Chilled Air," Cryobiology 27, 1990, pp. 189-193.
Shephard, R. J. "Adaptation to Exercise in the Cold," Sports Medicine, vol. 2, 1985, pp. 59-71.
Sigma-Aldrich "Poly(ethylene glycol) and Poly(ethylene oxide)," http://www.sigmaaldrich.com/materials-science/materialscience-;products.htmi?TablePage=2020411 0, accessed Oct. 19, 2012.
Smalls, L. K. et al. "Quantitative Model of Cellulite: Three Dimensional Skin Surface Topography, Biophysical Characterization, and Relationship to Human Perception," International Journal of Cosmetic Science, vol. 27, Issue 5, Oct. 2005, 17 pgs.
Thermage, News Release, "Study Published in Facial Plastic Surgery Journal Finds Selective Heating of Fibrous Septae Key to Success and Safety of Thermage ThermaCool System," Jun. 20, 2005, 2 pages.
ThermaCool Monopolar Capacitive Radiofrequency, The one choice for nonablative tissue tightening and contouring, Thermage, Inc. Tech Brochure, Nov. 30, 2005, 8 pgs.
Vallerand et al. "Cold Stress Increases Lipolysis, FFA Ra and TG/FFA Cycling in Humans," Aviation, Space, and Environmental Medicine 70(1), 1999, pp. 42-50.
Wang, X. et al., "Cryopreservation of Cell/Hydrogel Constructs Based on a new Cell-Assembling Technique," Sep. 5, 2009, 40 pages.
Wharton, D. A. et al., "Cold Acclimation and Cryoprotectants in a Freeze-Tolerant Antarctic Nematode, Panagrolaimus Davidi,", Journal of Comparative Physiology, vol. 170, No. 4, Mar. 2000, 2 pages.
Winkler, C. et al., "Gene Transfer in Laboratory Fish: Model Organisms for the Analysis of Gene Function," in Transgenic Animals, Generation and Use (The Netherlands 1997), pp. 387-395.
Young, H. E. et al. "Isolation of Embryonic Chick Myosatellite and Pluripotent Stem Cells" The Journal of Tissue Culture Methods, vol. 14, Issue 2, 1992, pp. 85-92.
Zelickson, B. et al., "Cryolipolysis for Noninvasive Fat Cell Destruction: Initial Results from a Pig Model", 35 Dermatol. Sug., 2009, pp. 1-9.
Zouboulis, C. C. et al., "Current Developments and Uses of Cryosurgery in the Treatment of Keloids and Hypertrophic Scars," Wound Repair and Regeneration, vol. 10, No. 2, 2002, pp. 98-102.
Examination Report for European Application No. 16790808.6; dated Oct. 31, 2019; 5 pages.

* cited by examiner

VASCULAR TREATMENT SYSTEMS, COOLING DEVICES, AND METHODS FOR COOLING VASCULAR STRUCTURES

CROSS-REFERENCE TO RELATED APPLICATION

The present application claims the benefit of and priority under 35 U.S.C. § 119(e) to U.S. Provisional Patent Application No. 62/243,529, filed Oct. 19, 2015, which is incorporated herein by reference in its entirety.

INCORPORATION BY REFERENCE OF COMMONLY-OWNED APPLICATIONS AND PATENTS

The following commonly assigned U.S. Patent Applications, U.S. patents, and International Publication are incorporated herein by reference in their entirety:

U.S. Patent Publication No. 2008/0287839 entitled "METHOD OF ENHANCED REMOVAL OF HEAT FROM SUBCUTANEOUS LIPID-RICH CELLS AND TREATMENT APPARATUS HAVING AN ACTUATOR";

U.S. Pat. No. 6,032,675 entitled "FREEZING METHOD FOR CONTROLLED REMOVAL OF FATTY TISSUE BY LIPOSUCTION";

U.S. Patent Publication No. 2007/0255362 entitled "CRYOPROTECTANT FOR USE WITH A TREATMENT DEVICE FOR IMPROVED COOLING OF SUBCUTANEOUS LIPID-RICH CELLS";

U.S. Pat. No. 7,854,754 entitled "COOLING DEVICE FOR REMOVING HEAT FROM SUBCUTANEOUS LIPID-RICH CELLS";

U.S. Pat. No. 8,337,539 entitled "COOLING DEVICE FOR REMOVING HEAT FROM SUBCUTANEOUS LIPID-RICH CELLS";

U.S. Patent Publication No. 2008/0077201 entitled "COOLING DEVICES WITH FLEXIBLE SENSORS";

U.S. Pat. No. 9,132,031 entitled "COOLING DEVICE HAVING A PLURALITY OF CONTROLLABLE COOLING ELEMENTS TO PROVIDE A PREDETERMINED COOLING PROFILE";

U.S. Patent Publication No. 2009/0118722, filed Oct. 31, 2007, entitled "METHOD AND APPARATUS FOR COOLING SUBCUTANEOUS LIPID-RICH CELLS OR TISSUE";

U.S. Patent Publication No. 2009/0018624 entitled "LIMITING USE OF DISPOSABLE SYSTEM PATIENT PROTECTION DEVICES";

U.S. Pat. No. 8,523,927 entitled "SYSTEM FOR TREATING LIPID-RICH REGIONS";

U.S. Patent Publication No. 2009/0018625 entitled "MANAGING SYSTEM TEMPERATURE TO REMOVE HEAT FROM LIPID-RICH REGIONS";

U.S. Patent Publication No. 2009/0018627 entitled "SECURE SYSTEMS FOR REMOVING HEAT FROM LIPID-RICH REGIONS";

U.S. Patent Publication No. 2009/0018626 entitled "USER INTERFACES FOR A SYSTEM THAT REMOVES HEAT FROM LIPID-RICH REGIONS";

U.S. Pat. No. 6,041,787 entitled "USE OF CRYOPROTECTIVE AGENT COMPOUNDS DURING CRYOSURGERY";

U.S. Pat. No. 8,285,390 entitled "MONITORING THE COOLING OF SUBCUTANEOUS LIPID-RICH CELLS, SUCH AS THE COOLING OF ADIPOSE TISSUE";

U.S. Pat. No. 8,275,442 entitled "TREATMENT PLANNING SYSTEMS AND METHODS FOR BODY CONTOURING APPLICATIONS";

U.S. patent application Ser. No. 12/275,002 entitled "APPARATUS WITH HYDROPHILIC RESERVOIRS FOR COOLING SUBCUTANEOUS LIPID-RICH CELLS";

U.S. patent application Ser. No. 12/275,014 entitled "APPARATUS WITH HYDROPHOBIC FILTERS FOR REMOVING HEAT FROM SUBCUTANEOUS LIPID-RICH CELLS";

U.S. Pat. No. 8,603,073 entitled "SYSTEMS AND METHODS WITH INTERRUPT/RESUME CAPABILITIES FOR TREATING SUBCUTANEOUS LIPID-RICH CELLS";

U.S. Pat. No. 8,192,474 entitled "TISSUE TREATMENT METHODS";

U.S. Pat. No. 8,702,774 entitled "DEVICE, SYSTEM AND METHOD FOR REMOVING HEAT FROM SUBCUTANEOUS LIPID-RICH CELLS";

U.S. Pat. No. 8,676,338 entitled "COMBINED MODALITY TREATMENT SYSTEMS, METHODS AND APPARATUS FOR BODY CONTOURING APPLICATIONS";

U.S. Patent Publication No. 2011/0238050 entitled "HOME-USE APPLICATORS FOR NON-INVASIVELY REMOVING HEAT FROM SUBCUTANEOUS LIPID-RICH CELLS VIA PHASE CHANGE COOLANTS, AND ASSOCIATED DEVICES, SYSTEMS AND METHODS";

U.S. Patent Publication No. 2011/0238051 entitled "HOME-USE APPLICATORS FOR NON-INVASIVELY REMOVING HEAT FROM SUBCUTANEOUS LIPID-RICH CELLS VIA PHASE CHANGE COOLANTS, AND ASSOCIATED DEVICES, SYSTEMS AND METHODS";

U.S. Patent Publication No. 2012/0239123 entitled "DEVICES, APPLICATION SYSTEMS AND METHODS WITH LOCALIZED HEAT FLUX ZONES FOR REMOVING HEAT FROM SUBCUTANEOUS LIPID-RICH CELLS";

U.S. Patent Publication No. 2014/0277219 entitled "MULTI-MODALITY TREATMENT SYSTEMS, METHODS AND APPARATUS FOR ALTERING SUBCUTANEOUS LIPID-RICH TISSUE";

U.S. Patent Publication No. 2014/0277302 entitled "TREATMENT SYSTEMS WITH FLUID MIXING SYSTEMS AND FLUID-COOLED APPLICATORS AND METHODS OF USING THE SAME";

U.S. Patent Publication No. 2013/0116759 entitled "COOLING DEVICE HAVING A PLURALITY OF CONTROLLABLE COOLING ELEMENTS TO PROVIDE A PREDETERMINED COOLING PROFILE;"

U.S. Patent Publication No. 2013/0116758 entitled "MONITORING THE COOLING OF SUBCUTANEOUS LIPID-RICH CELLS, SUCH AS THE COOLING OF ADIPOSE TISSUE;"

U.S. Patent Publication No. 2013/0158636 entitled "COOLING DEVICE FOR REMOVING HEAT FROM SUBCUTANEOUS LIPID-RICH CELLS;"

U.S. Patent Publication No. 2013/0066309 entitled "TISSUE TREATMENT METHODS;"

U.S. patent application Ser. No. 14/808,245 entitled "TISSUE TREATMENT METHODS;"

U.S. patent application Ser. No. 14/825,841 entitled "COOLING DEVICE HAVING A PLURALITY OF CONTROLLABLE COOLING ELEMENTS TO PROVIDE A PREDETERMINED COOLING PROFILE;"

U.S. Patent Publication No. 2014/0005760 entitled "CRYOPROTECTANT FOR USE WITH A TREATMENT DEVICE FOR IMPROVED COOLING OF SUBCUTANEOUS LIPID-RICH CELLS;"

U.S. Patent Publication No. 2013/0079684 entitled "METHOD OF ENHANCED REMOVAL OF HEAT FROM SUBCUTANEOUS LIPID-RICH CELLS AND TREATMENT APPARATUS HAVING AN ACTUATOR;"

U.S. Patent Publication No. 2014/0067025 entitled "SYSTEM FOR TREATING LIPID-RICH SYSTEMS;"

U.S. Patent Publication No. 2014/0316393 entitled "COMBINED MODALITY TREATMENT SYSTEMS, METHODS AND APPARATUS FOR BODY CONTOURING APPLICATIONS;"

U.S. Patent Publication No. 2013/0245731 entitled "SYSTEMS AND METHODS WITH INTERRUPT/RESUME CAPABILITIES FOR TREATING SUBCUTANEOUS LIPID-RICH CELLS;"

U.S. Patent Publication No. 2014/0257443 entitled "DEVICE, SYSTEM AND METHOD OF REMOVING HEAT FROM SUBCUTANEOUS LIPID-RICH CELLS;"

U.S. Patent Publication No. 2015/0216720 entitled "TREATMENT SYSTEMS, METHODS, AND APPARATUSES FOR IMPROVING THE APPEARANCE OF SKIN AND PROVIDING FOR OTHER TREATMENTS;"

U.S. Patent Publication No. 2015/0216816 entitled "COMPOSITIONS, TREATMENT SYSTEMS AND METHODS FOR IMPROVED COOLING OF LIPID-RICH TISSUE;"

U.S. Patent Publication No. 2015/0216719 entitled "TREATMENT SYSTEMS AND METHODS FOR TREATING CELLULITE AND FOR PROVIDING OTHER TREATMENTS;"

U.S. patent application Ser. No. 14/662,181 entitled "TREATMENT SYSTEMS, DEVICES, AND METHODS FOR COOLING TARGETED TISSUE;"

U.S. patent application Ser. No. 14/710,407 entitled "TREATMENT SYSTEMS WITH ADJUSTABLE GAP APPLICATORS AND METHODS FOR COOLING TISSUE;"

U.S. patent application Ser. No. 14/705,868 entitled "TREATMENT SYSTEMS, SMALL VOLUME APPLICATORS, AND METHODS FOR TREATING SUBMENTAL TISSUE;"

U.S. patent application Ser. No. 14/829,424 entitled "STRESS RELIEF COUPLINGS FOR CRYOTHERAPY APPARATUSES;"

U.S. patent application Ser. No. 14/855,017 entitled "TREATMENT SYSTEMS, METHODS, AND APPARATUSES FOR ALTERING THE APPEARANCE OF SKIN;"

International Publication No. 2015/117032 entitled "TREATMENT SYSTEMS AND METHODS FOR AFFECTING GLANDS AND OTHER TARGETED STRUCTURES;"

U.S. Provisional Patent Application No. 62/153,896 entitled "SYSTEMS AND METHODS FOR MONITORING COOLING OF SKIN AND TISSUE TO IDENTIFY FREEZE EVENTS;" and U.S. Provisional Patent Application No. 62/221,490 entitled "TRANSCUTANEOUS TREATMENT SYSTEMS, COOLING DEVICES, AND METHOD FOR COOLING NERVES."

TECHNICAL FIELD

The present disclosure relates generally to treatment systems, cooling devices, and methods for cooling vascular structures. In particular, several embodiments are directed to vascular treatment systems, thermoelectric devices, and methods for reducing or eliminating vascular irregularities located along a subject's skin and for performing other treatments.

BACKGROUND

Port wine stains, hemangioma, telangiectasia, vascular malformations, and other tissue anomalies are often considered visually unappealing and difficult to treat. For example, port wine stains are defects caused by enlarged, ectatic dermal blood vessels that result in pink, red, or purple cutaneous lesions, typically present at birth. Hemangioma is a benign tumor formed by abnormal blood vessels, which often produce a red birthmark on or under the surface of the skin. Telangiectasia refers to a collection of visible dilated cutaneous blood vessels often located near the surface of the skin. Vascular malformations, such as dilated blood vessels, are often visible to the naked eye.

In conventional light-based therapies, light from a laser or a flashlamp is used to coagulate blood in abnormal vascular structures and/or to thermally injure blood vessel. For example, lasers can generate enough heat to burn tissue (e.g., to destroy targeted blood vessels), resulting in an improved appearance. Essentially, lasers burn tissue. Unfortunately, the heat generated during conventional light therapies may cause significant discomfort or pain during and after the treatment session, as well as undesired pigmentation alteration (e.g., temporary reddening, permanent hyperpigmentation or hypopigmentation, etc.), blistering (e.g., blistering due to heat-induced separation between dermal and epidermal layers), and scarring. Additionally, equipment for performing light-based procedures is expensive and often requires frequent complicated calibration, resulting in high operating costs. To limit adverse effects, trained personnel are required to operate the equipment, due to difficulty in controlling dosage and difficulty in visually inspecting a treatment site and determining whether clinical endpoints have been reached. Accordingly, there is a need for more effective treatments of skin irregularities caused by vascular malformations and other tissue conditions.

BRIEF DESCRIPTION OF THE DRAWINGS

In the drawings, identical reference numbers identify similar elements or acts.

DETAILED DESCRIPTION

A. Overview

Figure 1:
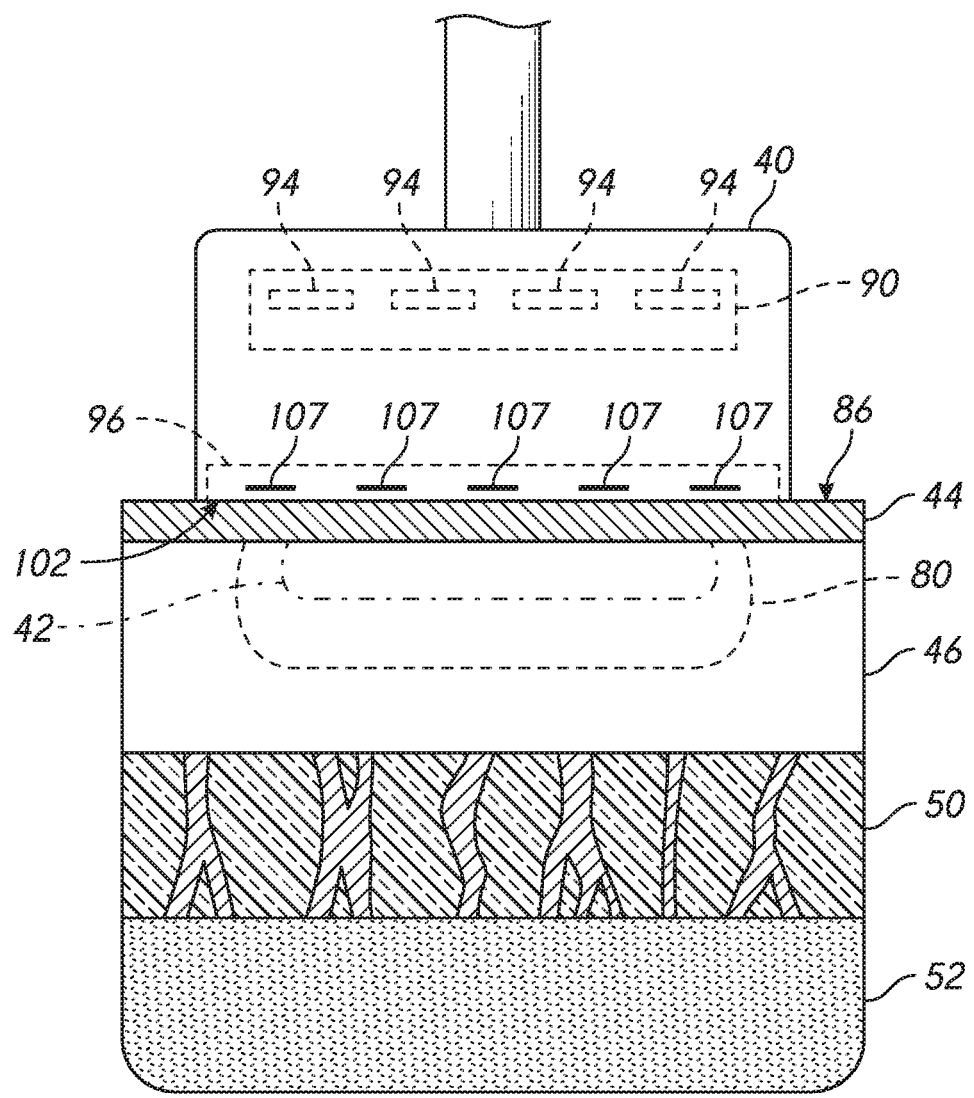
FIG. 1 is a schematic cross-sectional view of tissue with a non-invasive applicator in thermal contact with an exposed surface of a subject's skin.

The present disclosure describes treatment systems and methods for treating features located along a subject's skin and at other locations. Some treatment methods can include applying a non-invasive applicator to a patient and transcutaneously cooling/heating tissue to reduce, eliminate, or otherwise alter targeted features to improve the appearance of a treatment site. The targeted features can be skin irregularities, malformations, or the like. Several of the details set forth below are provided to describe the following examples and methods in a manner sufficient to enable a person skilled in the relevant art to practice, make, and use them. Several of the details and advantages described below, however, may not be necessary to practice certain examples and methods of the technology. Additionally, the technology may include other examples and methods that are within the scope of the technology but are not described in detail.

At least some embodiments are directed to reducing or eliminating skin irregularities considered to be visually unappealing. The skin irregularities can be port wine stains, a collection of irregular blood vessels, vascular malformations, or the like. Cold therapy can be used to lighten or reduce the visibility (e.g., visibility to the naked eye) of the skin irregularities by, for example, destroying target vascular structures, constricting blood vessels, and/or reducing blood flow associated with the skin irregularities. Cooling/heating of the subject's skin can be controlled to achieve the desired effect. To treat a port wine stain, the subject's skin can be cooled to a temperature low enough to reduce ectatic blood vessels and thereby lighten the port wine stain. The cooling/heating profile and severity and number of treatments can be selected based on the characteristics of the port wine stain and the desired visual appearance of the target site.

Various aspects of the technology are directed to devices that cool/heat a target region for a period of time selected to localize thermal effects to affect targeted structures. The devices can be thermoelectric devices capable of cooling targeted vascular structures to a temperature low enough and for a period of time long enough so as to substantially affect the vascular structures. The skin surface and/or targeted structures can be cooled to a temperature equal to or lower than about −40° C., −35° C., −30° C., −25° C., −20° C., −15° C., −10° C., −5° C., −2° C., or −1° C. for a treatment period equal to or longer than about 30 seconds, 1 minute, 2 minutes, 3 minutes, 4 minutes, 5 minutes, 7 minutes, 10 minutes, 12 minutes, 15 minutes, 30 minutes, 45 minutes, or 1 hour. In some procedures, the skin surface is cooled to a temperature lower than about −5° C. and higher than about −25° C. or −30° C. for about 2 minutes to about 20 minutes. Target vascular structures directly below the cooled skin can be thermally injured, destroyed, or otherwise altered. For example, a majority of the blood vessels of a visible vascular malformation can be destroyed via cold injury. In other procedures, the treatment period can be shorter than about 30 seconds, or shorter than or equal to about 1, 2, 3, 4, 5, 7, 10, 15, 20, 25, 30, 35, 40, 45, 50, or 55 minutes, or shorter than or equal to about 1 or 2 hours. Cold therapy at these treatment temperatures and treatment times using transcutaneous cooling devices can be effective in damaging blood vessel cells so as to significantly injure the blood vessels, especially when the cooling device is applied with sufficient pressure to reduce or limit blood flow in the vessels so as to maximize a cooling effect on the cells from the cooling device. Applied pressure can prevent or limit warm blood flow from heating or otherwise preventing the cooling device from cooling the vessel cells. The cold therapy can be controlled to either produce a freeze or non-freeze injury.

When treating certain regions (e.g., regions along the face), it is often undesirable to unduly injure the epidermis, subcutaneous fat, or facial muscle. In an extreme case, if the epidermis is overly frozen or damaged, hyperpigmentation (skin darkening) or hypopigmentation (skin lightening) can result, which is often undesirable. Cryoprotectants, heating (e.g., periodic heating cycles in between cooling cycles or at the end of a single cooling cycle) and other techniques can be used to protect the epidermis (or other non-targeted tissue) to avoid, minimize, or limit hyperpigmentation and/or hypopigmentation either immediately after the treatment or hours, a day, days, or weeks thereafter. Additionally or alternatively, devices can have a temperature-controlled surface sized and configured to transcutaneously cool vascular structures (e.g., dermal blood vessels) while minimizing or limiting cold injury to non-targeted tissue, such as epidermal tissue. Cryoprotectants can be applied to the subject's skin to inhibit or prevent freezing of non-targeted tissue, such as epidermal tissue, where the cryoprotectant is absorbed, while allowing deeper tissue with reduced or no concentration of cryoprotectant to freeze and be more damaged than the epidermal tissue. The shape, configuration, thermal properties, and cooling capabilities of the applicator can be selected based on characteristics of the treatment site, targeted structures, etc.

A treatment session can include different procedures for treating different treatment sites. For example, a first procedure can be performed to reduce the visibility of a port wine stain, and the same or different procedure can be used to treat vascular malformations, such as spider veins, at another site. Conformable or contoured thermoelectric devices can be applied to highly contoured regions around, for example, the eyes, face, neck, etc. Non-conformable and flat applicators can be used for sites which are relatively flat. Treatment systems can also have multiple thermoelectric devices, each configured to be sequentially or concurrently applied at specific locations along the subject's body.

Some aspects of the technology are directed to treatment methods that include producing one or more freeze zones that affect targeted structures. The freeze zones can be located in one or more layers of tissue. The location, severity, and extent of freeze injury can be controlled to achieve the desired alteration. For example, a sufficient number of blood vessels can be injured to reduce the visibility of the blood vessels. In certain procedures, a majority or substantially all of the injured blood vessels can be part of a visible vascular structure which is being targeted. Blood vessels can be destroyed, injured, and/or sufficiently affected so that the treatment site has a normal, healthy appearance. In some procedures, blood vessels that supply blood to a target vascular structure can be cooled to cause constriction so as to reduce the flow rate of blood into the target vascular structure. This process can reduce the visibility of the vascular structure. Non-targeted tissue (e.g., subcutaneous fat or other tissue) can be substantially unaffected by the therapy, or affected to a lesser extent than the target vascular structure in the skin. The number of treatment sessions and severity of desired thermal effects can be selected based on characteristics of the target tissue, location of the treatment region (e.g., along face, neck, back, legs, etc.), and/or desired effect. Any number of treatments can be performed to address post-treatment vascular recurrence, such as blood vessel recurrence.

In some non-invasive procedures, one or more treatment regions can be transcutaneously cooled to reduce the visibility of vascular formation. In some procedures, blood vessels can be injured to inhibit blood flow into a targeted vascular structure. Additionally or alternatively, target structures that are part of a vascular formation can be transcutaneously cooled and injured to reduce the number and/or sizes of the target structures. Advantageously, non-invasive procedures can be performed to improve the appearance of the treatment site while avoiding, minimizing, or limiting problems often caused by conventional light therapies, such as laser therapy. For example, non-invasive procedures disclosed herein can be performed without causing pain, blistering, or other problems caused by heat generation associated with light therapy.

Some embodiments disclosed herein can be used for cosmetically beneficial alterations. For example, some treatment procedures may be for the sole purpose of altering a treatment region to achieve a cosmetically desirable look or other desirable cosmetic characteristic. Accordingly, at least some embodiments of the cosmetic procedures can be performed without providing any therapeutic effect or, in another embodiment, providing minimal therapeutic effect. For example, skin treatment procedures can be performed without restoring health, physical integrity, or the physical well-being of a subject. By isolating the thermal injury to the skin, deeper tissue can be unaffected or affected to a lesser extent than the targeted structures. Advantageously, treatments can be performed without visually inspecting the treatment site. Additionally, an applicator can monitor the treatment site, if desired, to maintain targeted treatment parameters.

A substance can be applied to the subject's skin to (a) provide thermal coupling between the subject's skin and cooling devices (e.g., cooling plates of cooling devices) to improve heat transfer therebetween, (b) selectively protect non-target tissues from freeze damage (e.g., damage due to crystallization), and/or (c) promote freeze events by increasing nucleation sites. The substance may be a fluid, a gel, or a paste and may be hygroscopic, thermally conductive, and biocompatible. In some embodiments, the substance can be a cryoprotectant that reduces or inhibits cell destruction. As used herein, "cryoprotectant," "cryoprotectant agent," and "composition" mean substances (e.g., compositions, formulations, compounds, etc.) that assist in preventing freezing of tissue compared to an absence of the substances(s). In one embodiment, the cryoprotectant allows, for example, the cooling device to be pre-cooled prior to being applied to the subject for more efficient treatment. Further, the cryoprotectant can also enable the device to be maintained at a desired low temperature while preventing ice from forming on a surface (e.g., heat-exchanging surface of an applicator). Yet another aspect of the technology is that the cryoprotectant may prevent the treatment device from freezing to the skin of the patient or subject. Additionally or alternatively, the cryoprotectant can allow microscopic crystals to form in the tissue but can limit crystal growth that would cause cell destruction, and in some embodiments, the cryoprotectant can allow for enhanced uptake or absorption and/or retention in target tissue prior to and during the introduction of cooling.

Reference throughout this specification to "one example," "an example," "one embodiment," or "an embodiment" means that a particular feature, structure, or characteristic described in connection with the example is included in at least one example of the present technology. Thus, the occurrences of the phrases "in one example," "in an example," "one embodiment," or "an embodiment" in various places throughout this specification are not necessarily all referring to the same example. The headings provided herein are for convenience only and are not intended to limit or interpret the scope or meaning of the technology.

B. Cryotherapy

FIG. 1 is a schematic cross-sectional view of tissue with a non-invasive applicator 40 applied to a treatment region. The applicator 40 can cool the subject's skin to a temperature low enough and for a period of time long enough so as to substantially affect and injure a target vascular structure 42 (shown in dot dashed line). The target vascular structure 42 may have significantly more blood vessels than the normal tissue has. Blood vessels can be thermally-injured to reduce the number of functioning blood vessels, to constrict blood vessels, or to otherwise reduce blood circulating at the treatment region. By normalizing circulating blood flow to match the blood flow of the surrounding normal tissue, the targeted vascular structure 42 can be reduced or eliminated to provide a normal appearance at the treatment site.

The illustrated target vascular structure 42 is located generally beneath the epidermis 44 and can include, for example, blood vessels, capillary vessels in the dermal layer 46, veins (e.g., varicose veins), vascular malformations, and/or other structures. For example, the target vascular structure 42 can be a port wine stain, which often has about 5× to 10× more blood vessels than surrounding normal tissue. One or more treatments can be performed to selectively destroy a sufficient number of blood vessels to achieve a desired reduction in visibility of the port wine stain. For example, if a port wine stain has about 5× more blood vessels than the surrounding normal tissue, the applicator 40 can be used to destroy about 80% of the blood vessels. As such, the port wine stain can be substantially eliminated so that the treatment has a generally healthy appearance. The target vascular structure 42 can also be located in other layers, such as the epidermis 44, connective layer 50, or subcutaneous tissue 52.

The applicator 40 can produce a cooling zone 80 (shown in dashed line) of tissue at or below a target temperature. The location, size, and depth of the cooling zone 80 can be selected to avoid injuring non-targeted tissue. In one procedure, the cooling zone 80 comprises most of the tissue directly between the targeted vascular structure 42 and the skin surface 86. Adjacent tissue may also be cooled but can be at a sufficiently high temperature to avoid permanent thermal injury. Additionally or alternatively, a cryoprotectant or other protective means can be used to inhibit thermal injury to non-targeted tissue. The target temperature for the zone 80 can be equal to or lower than −40° C., −30° C., −20° C., −10° C., −5° C., −3° C., 0° C., 2° C., 5° C., or the like.

The applicator 40 can include a thermal element 90, temperature-controlled surface 102, and sensors 107. The thermal element 90 can include, without limitation, thermoelectric elements, fluid channels through which coolant flows, resistive heaters, energy emitters, and/or other elements capable of heating and/or cooling. In some embodiments, the thermal element 90 includes Peltier device(s) 94 (e.g., a single Peltier element, an array of Peltier elements, etc.), or the like. A heat-exchanging plate 96 can facilitate heat transfer between the thermal element 90 and the skin surface 86. In non-thermoelectric embodiments, the thermal element 90 can include fluid channels for cooling/heating using only temperature-controlled liquid.

The temperature-controlled surface 102 can be part of the heat-exchanging plate 96, a separate metal surface, or other suitable surface. In one embodiment, the surface 102 can be the surface of an interface layer. The area of the surface 102 can be equal to or larger than about 2 $cm^2$, 3 $cm^2$, 4 $cm^2$, 5 $cm^2$, 6 $cm^2$, 7 $cm^2$, 8 $cm^2$, 9 $cm^2$, 10 $cm^2$, 12 $cm^2$, 15 $cm^2$, 20 $cm^2$, or 25 $cm^2$ to limit the size (e.g., width, depth, etc.) of the cooling zone 80. The temperature-controlled surface 102 can have a polygonal shape, a circular shape, an elongated shape (e.g., elliptical shape), or other shape selected to provide the desired cooling zone.

The sensors 107 can be configured to monitor temperatures, applied forces, and/or tissue contact. In some embodiments, the sensors 107 can be temperature sensors, pressure sensors, contact sensors, or other detection elements. The number and types of sensors can be selected based on the location and characteristics of the targeted features.

The effect of cooling blood vessels can be the selective injury, damage, reduction, and/or thickening of the walls of blood vessels. In some procedures, the applicator 40 can cool the exposed skin surface and/or the targeted structures to a temperature in a range from about −50° C. to about 10° C., about −40° C. to about −2° C., about −25° C. to about 0° C., about −25° C. to about −5° C., about −20° C. to about −5° C., or other suitable temperature ranges. In some treatments, the exposed skin surface can be at a temperature less than about −5° C. and greater than about −25° C. or −30° C. The treatment region can be cooled/heated any number of times. Periods of heating/cooling can be equal to or shorter than about 1 minute, 2 minutes, 3 minutes, 4 minutes, 5 minutes, 10 minutes, 20 minutes, 30 minutes, 40 minutes, 50 minutes, 1 hour, 90 minutes, 2 hours, etc. In one procedure, the treatment region can be continuously or intermittently cooled for a cooling period to injure blood vessels, and then continuously or intermittently heated for a heating period to further injure the blood vessels.

One expected advantage of techniques disclosed herein is that vascular features visible to the naked eye can be selectively reduced or eliminated due to a reduction in the volume of blood contained in the vascular features. The cold injury to the vascular features can be a non-freezing injury or a freezing injury. During procedures that require sustained exposure to cold temperatures, methods of protecting the overlying tissue (typically epidermal skin cells overlying the target vascular features) from freeze damage may include improving the freeze tolerance and/or freeze avoidance of these cells by applying cryoprotectant to zones where freeze protection is desired. For example, cryoprotectants can be topically applied to inhibit or prevent freeze damage to tissue between the cooled surface 102 and the target vascular structure 42. Additionally, or alternatively, periodic heating can be used to protect shallow non-targeted tissue.

C. Treatment Systems

Figure 2:
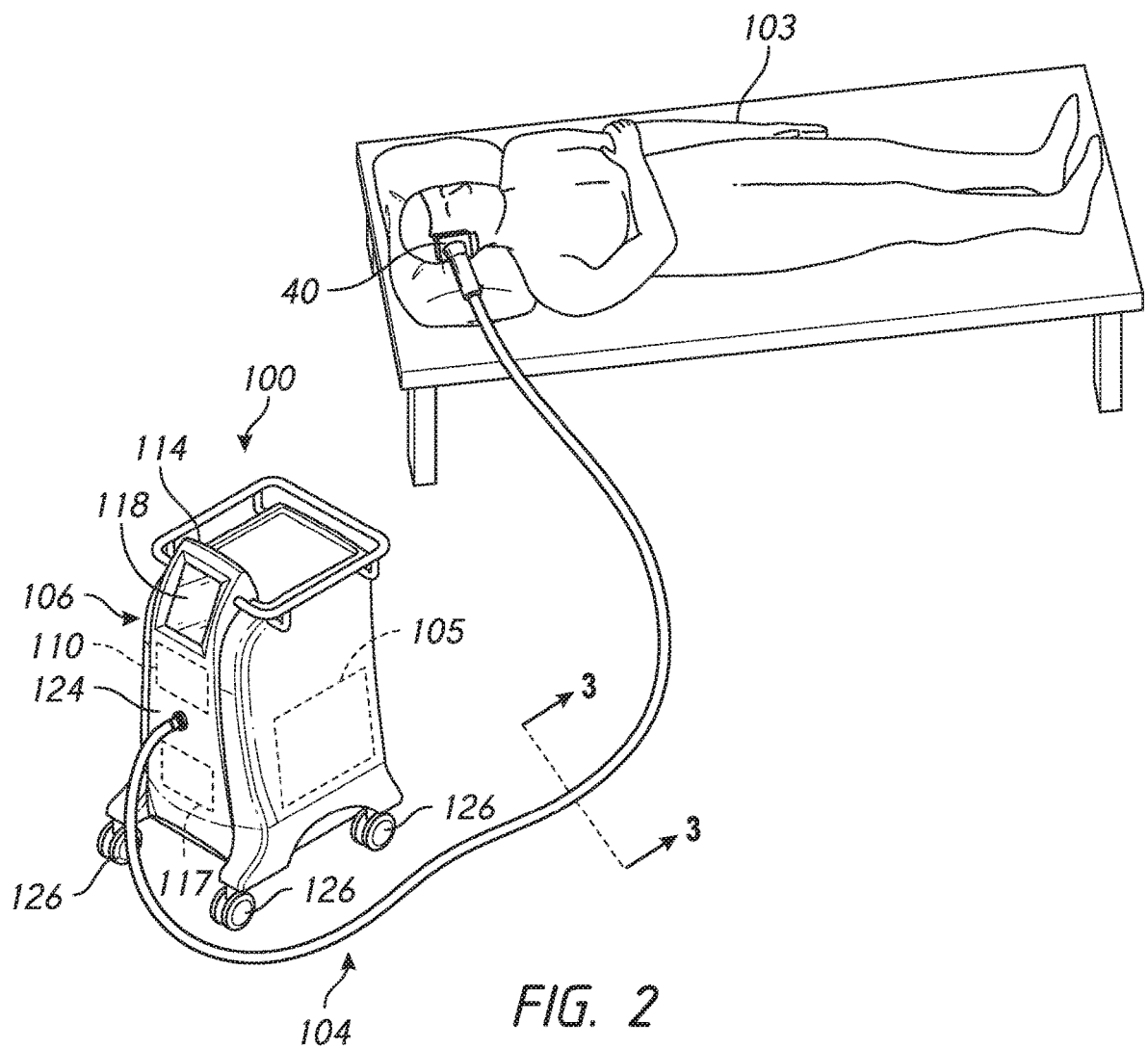
FIG. 2 is a partially schematic, isometric view of a treatment system for treating an area of the subject's skin in accordance with an embodiment of the technology.

FIG. 2 shows a treatment system 100 that includes the applicator 40, a connector 104, and a control module 106. The subject 103 or operator can manually hold the applicator 40 against the subject 103. Alternatively, restraining means can hold the applicator 40 against the subject 103 and can be, for example, a strap system, a helmet, or the like. The connector 104 can provide energy (e.g., electrical energy) and fluid (e.g., coolant) from the control module 106 to the applicator 40. An operator can use the control module 106 to control operation of the applicator 40.

Figure 3:
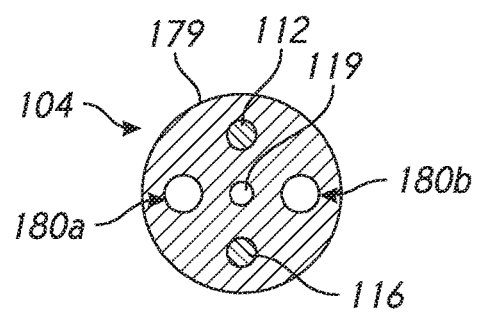
FIG. 3 is a cross-sectional view of a connector taken along line 3-3 of FIG. 2.

FIG. 3 is a cross-sectional view of the connector 104 taken along line 3-3 of FIG. 2 in accordance with at least some embodiments of the technology. The connector 104 can include a main body 179, a supply fluid line or lumen 180a ("supply fluid line 180a"), and a return fluid line or lumen 180b ("return fluid line 180b"). The main body 179 may be configured (via one or more adjustable joints) to "set" in place for the treatment of the subject 103. The supply and return fluid lines 180a, 180b can be conduits comprising, in whole or in part, polyethylene, polyvinyl chloride, polyurethane, and/or other materials that can accommodate circulating coolant, such as water, glycol, synthetic heat transfer fluid, oil, refrigerant, and/or any other suitable heat-conducting fluid. In one embodiment, each fluid line 180a, 180b can be a flexible hose surrounded by the main body 179. The connector 104 can also include one or more electrical lines 112 for providing power to the applicator 40 and one or more control lines 116 for providing communication between the control module 106 (FIG. 2) and the applicator 40 (FIGS. 1 and 2). In various embodiments, the connector 104 can include a bundle of fluid conduits, a bundle of power lines, wired connections, and other bundled and/or unbundled components selected to provide ergonomic comfort, minimize unwanted motion (and thus potential inefficient removal of heat from the subject 103), and/or to provide a pleasing aesthetic appearance to the treatment system 100.

Referring again to FIG. 2, the control module 106 can include a fluid chamber or reservoir 105 (illustrated in phantom line), a power supply 110 (illustrated in phantom line), and a controller 114 carried by a housing 124 with wheels 126. The control module 106 can include a refrigeration unit, a cooling tower, a thermoelectric chiller, heaters, or any other device capable of controlling the temperature of coolant in the fluid chamber 105. The coolant can be continuously or intermittently delivered to the applicator 40 via the supply fluid line 180a (FIG. 3) and can circulate through the applicator 40 to absorb heat. For example, the applicator 40 can be a thermoelectric device through which the coolant flows to cool components of the applicator 40. The coolant, which has absorbed heat, can flow from the applicator 40 back to the control module 106 via the return fluid line 180b (FIG. 3). For warming periods, the control module 106 can heat the coolant such that warm coolant is circulated through the applicator 40. Alternatively, a municipal water supply (e.g., tap water) can be used in place of or in conjunction with the control module 106.

A pressurization device 117 can provide suction via a vacuum line 119 (FIG. 3) and can include one or more pumps. A vacuum can be used to draw the subject's skin against the applicator 40. Air pressure can either be controlled with a regulator between the pressurization device 117 and the applicator 40, or pressure may be reduced up to the maximum capacity of the pressurization device 117. In other embodiments, the applicator 40 may not provide any vacuum.

An operator can control operation of the treatment system 100 using an input/output device 118 of the controller 114. The controller 114 can be programmed to modify operation of the applicator 40 based upon temperature at the treatment region, applied pressure, and/or other monitored parameters. The input/output device 118 can display the status of the procedure (e.g., percentage of procedure completed), the state of operation of the applicator 40 or other information. The power supply 110 can provide a direct current voltage for powering electrical elements of the applicator 40 via the electrical line 112 (FIG. 3). In some embodiments, the controller 114 can exchange data with the applicator 40 via a wireless or an optical communication link and can monitor and adjust treatment based on one or more treatment profiles and/or patient-specific treatment plans, such as those described, for example, in commonly assigned U.S. Pat. No. 8,275,442. Each treatment profile can include one or more segments, and each segment can include specified durations (e.g., 1 minute, 2 minutes, 3 minutes, 4 minutes, 5 minutes, 7 minutes, 10 minutes, 15 minutes, 20 minutes, 30 minutes, 1 hour, 2 hours, etc.), a target profile, etc. Treatment profiles can be selected based upon the targeted treatment site. For example, treatment profiles to lighten port wine stains may be different from treatment profiles for long-lasting or permanent lightening of spider veins. An operator can monitor and control thermal parameters, including (1) cooling rate, (2) end (e.g., minimum) temperature, (3) time held at the minimum temperature (e.g., hold time), (4) temperature profiles, and/or (5) warming or thawing rates.

D. Methods of Treatment

Figure 4A:
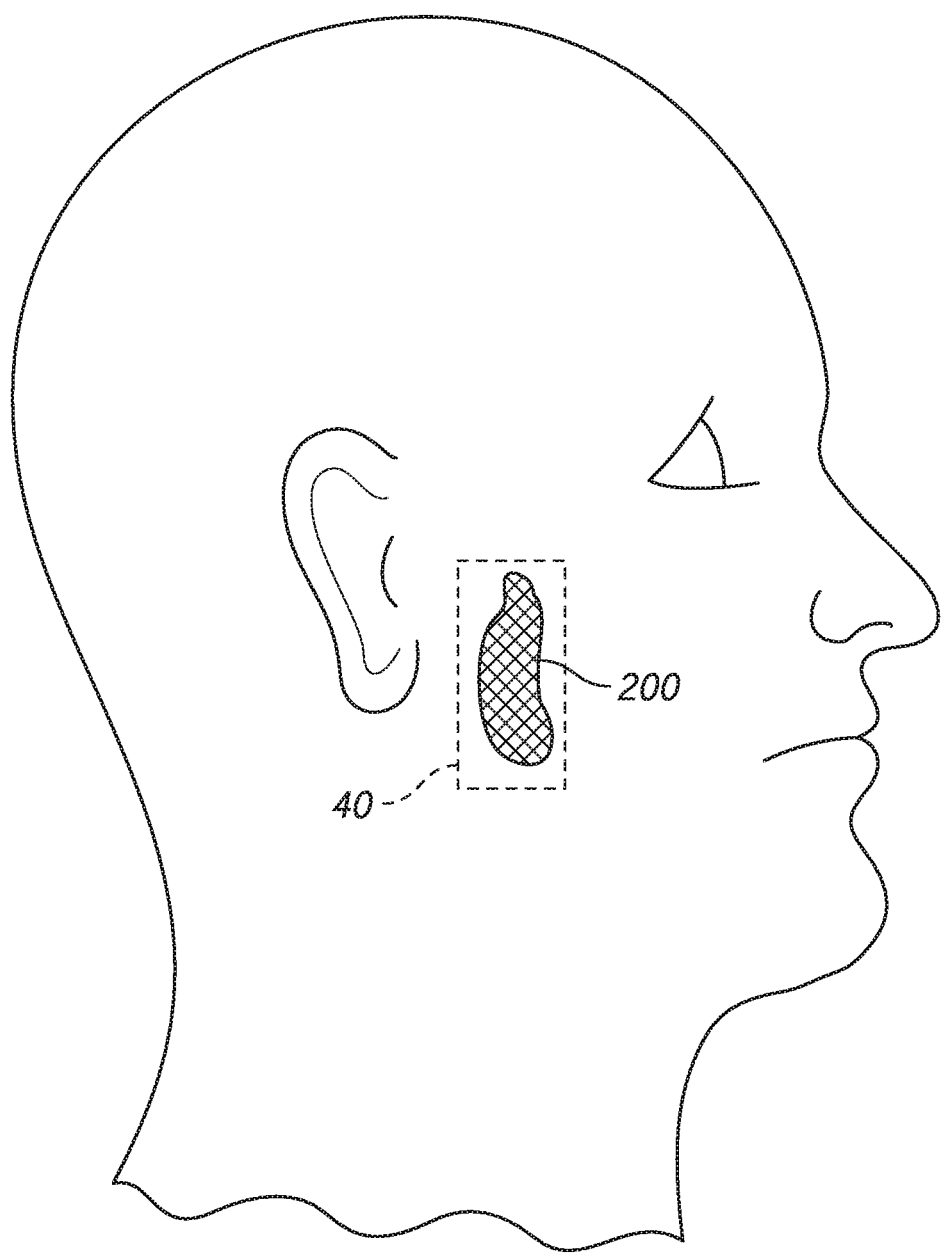
FIGS. 4A-4C illustrate a method of treating a targeted anomaly in accordance with an embodiment of the technology.
Figure 4B:
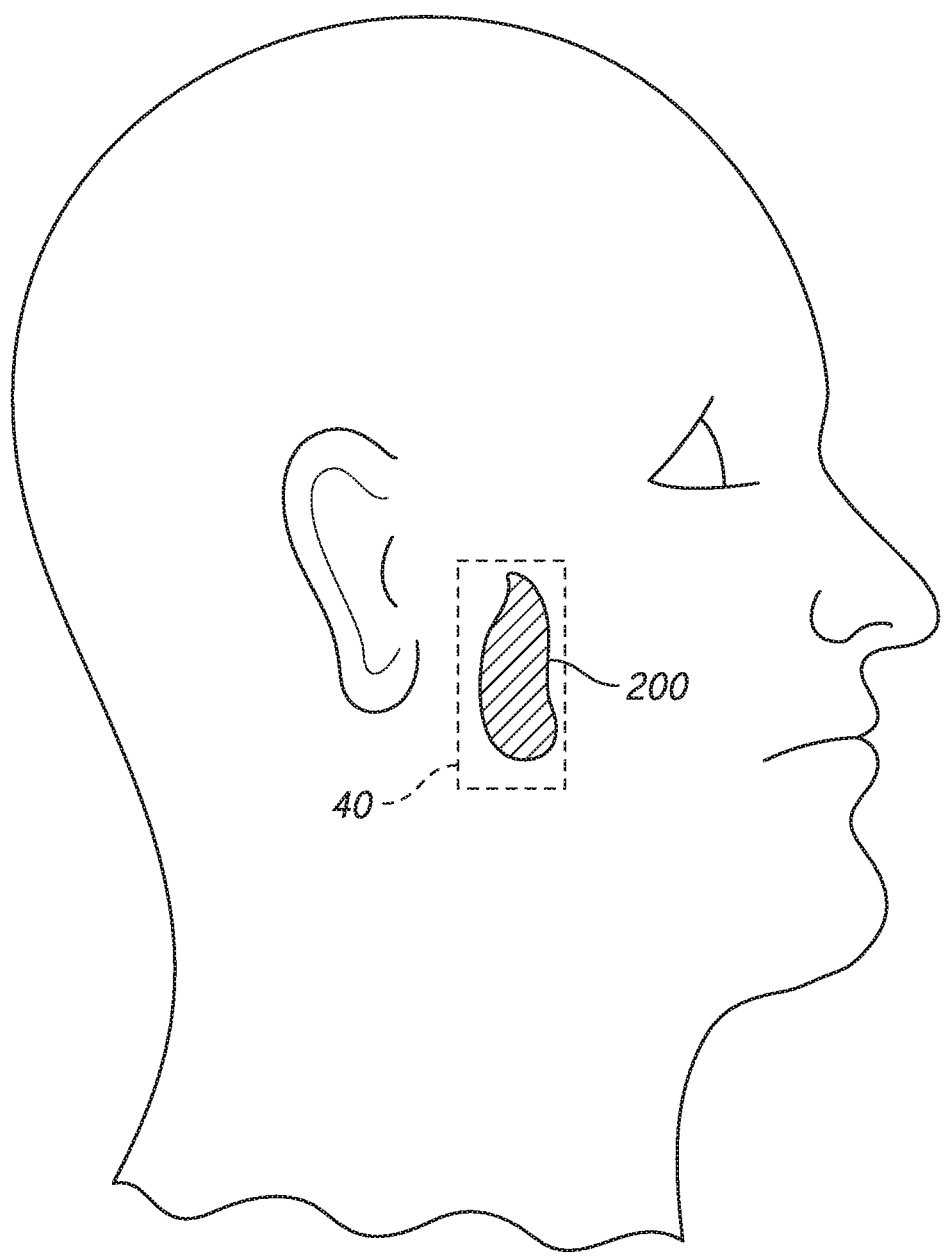
Figure 4C:
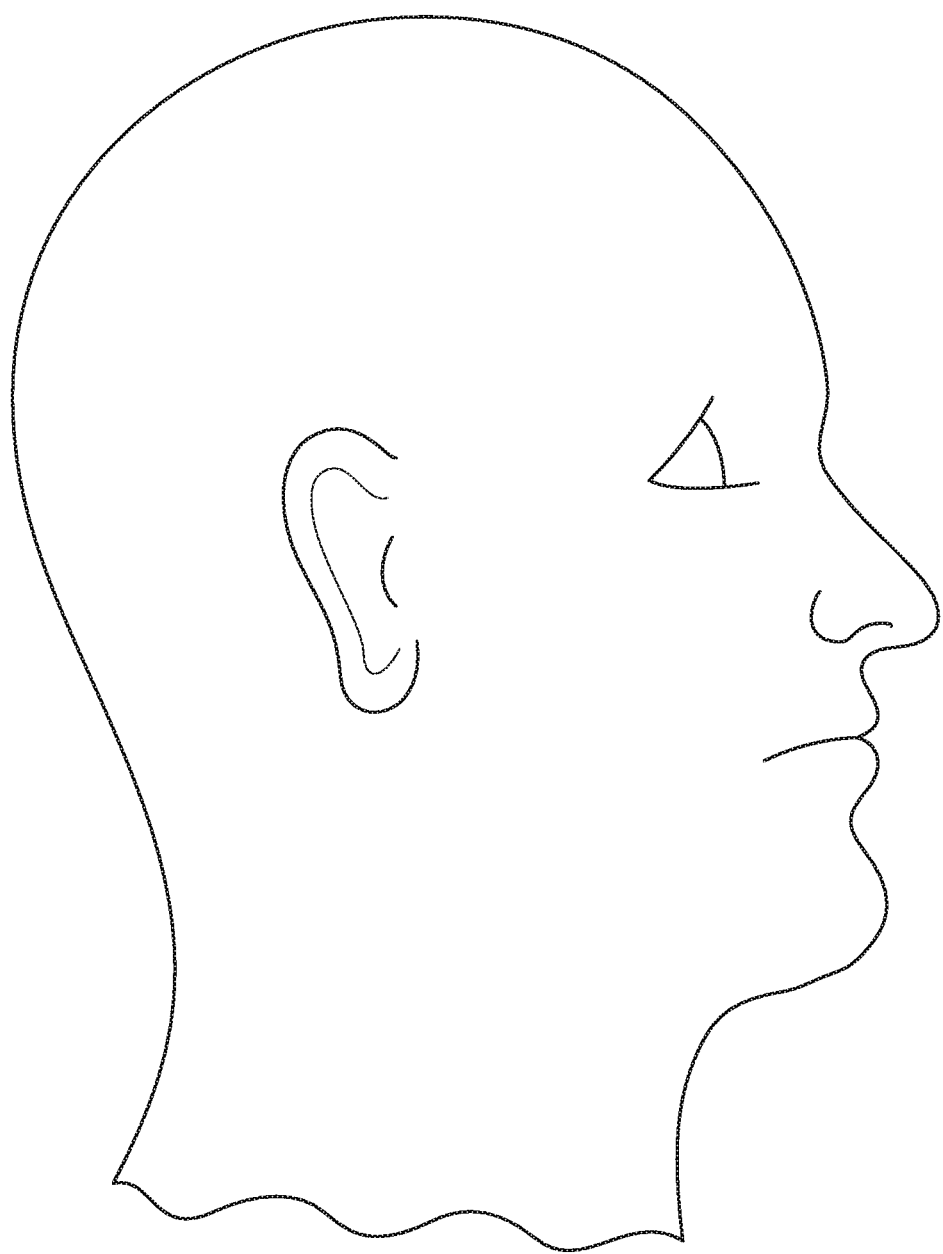

FIGS. 4A-4C illustrate a method of treating a targeted area in accordance with an embodiment of the technology. FIGS. 5A-5E illustrate another method of treating a targeted area. Generally, the subject's skin can be cooled to a temperature low enough to maintain a cooled state or frozen state for a period of time long enough to affect targeted structures. The characteristics of the event (e.g., cooling event or freeze event) can be controlled to manage thermal effects. Such characteristics can include, without limitation, the amount of cooling or freezing, density and distribution of ice crystals, freezing rate, etc. Freeze events can include partially or completely freezing tissue and/or structures to destroy, reduce, disrupt, modify, or otherwise affect targeted structures or the supporting anatomical features, such as supporting vascular structures. In some procedures, to treat skin vascular malformations, a subject's skin can be cooled to produce a localized partial freeze event in a portion of skin with vascular malformations. The level of freezing can be controlled to manage tissue damage (if any) to non-targeted tissue, damage of targeted tissue (e.g., to avoid excess damage to targeted tissue), and so forth. The subject's skin can be continuously or periodically cooled/heated to adjust the level of freezing. For example, the skin surface can be cooled or heated to increase or decrease, respectively, the number and/or sizes of ice crystals at the target region. Details of specific procedures are discussed in connection with FIGS. 4A to 5E.

FIG. 4A illustrates a facial vascular structure or anomaly 200 that can be treated in accordance with embodiments of the disclosure. The applicator 40 (shown in phantom line) can overlay the highly visible facial vascular structure 200 that may have an unattractive appearance. The facial vascular anomaly 200 can be, for example, a vascular malformation, a network or collection of abnormal blood vessels, a port wine stain, a group of relatively large capillary vessels, and so forth. The vascular structure 200, for example, can occupy more than 50%, 60%, 70%, 80%, 90%, or 99% of an area of the treatment region to be cooled.

The applicator 40 can apply sufficient pressure to reduce, limit, or eliminate blood flow to and/or through the targeted vascular anomaly 200 to improve cooling efficiency because blood circulation is one mechanism for maintaining a constant body temperature. Blood flow through the epidermis, dermis, and subcutaneous tissue is a heat source that can counteract the cooling of the vascular anomaly 200. If the blood flow is not reduced, cooling the vascular anomaly 200 would require not only removing the specific heat of the vascular tissue (e.g., walls of the vessels) but also that of the blood circulating through the vascular vessels. Thus, reducing or eliminating blood flow through the vascular anomaly 200 can improve the efficiency of cooling of the vessel walls. In some procedures, the applied pressure can be greater than or equal to systolic blood pressure in the skin. The applied pressure, for example, may be higher than the systolic pressure to impede or block the blood flow into and through the vascular anomaly 200 before, during, and/or after cooling. In some embodiments, one or more straps, restraints, and/or harnesses can be used to hold the applicator 40 firmly against the treatment region to maintain a threshold pressure sufficient to inhibit blood flow through the vascular anomaly 200.

The applicator 40 can also detect partial or total freeze events in the patient's tissue. After detecting the partial or total freeze event, the applicator 40 can operate to maintain a partially or totally frozen state of the tissue for a period of time long enough to alter targeted vascular structures. In one embodiment, the period of time is longer than a predetermined threshold period of time, such as 10 seconds, 20 seconds, 1 minute, or other selected period of time. If the epidermis is overly frozen, hyperpigmentation (skin darkening) or hypopigmentation (skin lightening) can result, which is often undesirable. The applicator 40 can be controlled so as to not cause hypopigmentation and/or hyperpigmentation more than a day following treatment.

FIG. 4B shows the treatment region after the vascular anomaly 200 has been lightened due to cold therapy. The applicator 40 can be used to further cool the vascular anomaly 200 to further reduce the visibility of the vascular anomaly 200 until it is not visible to the naked eye. FIG. 4C shows the subject after the vascular structures at the treatment region have been sufficiently altered to match the vascular structures in the surrounding healthy tissue.

Figure 5A:
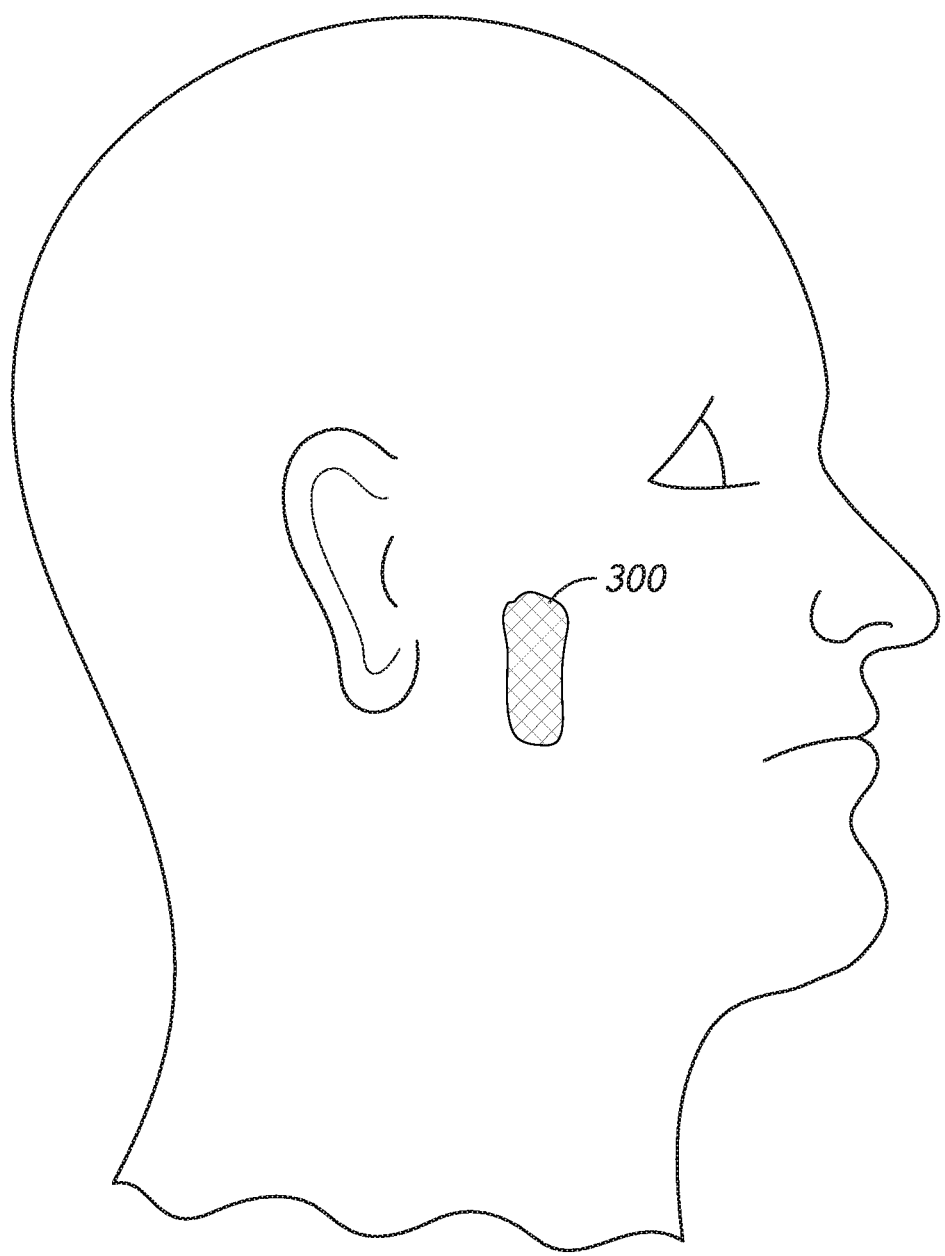
FIG. 5A illustrates a skin anomaly located along a subject's face.
Figure 5B:
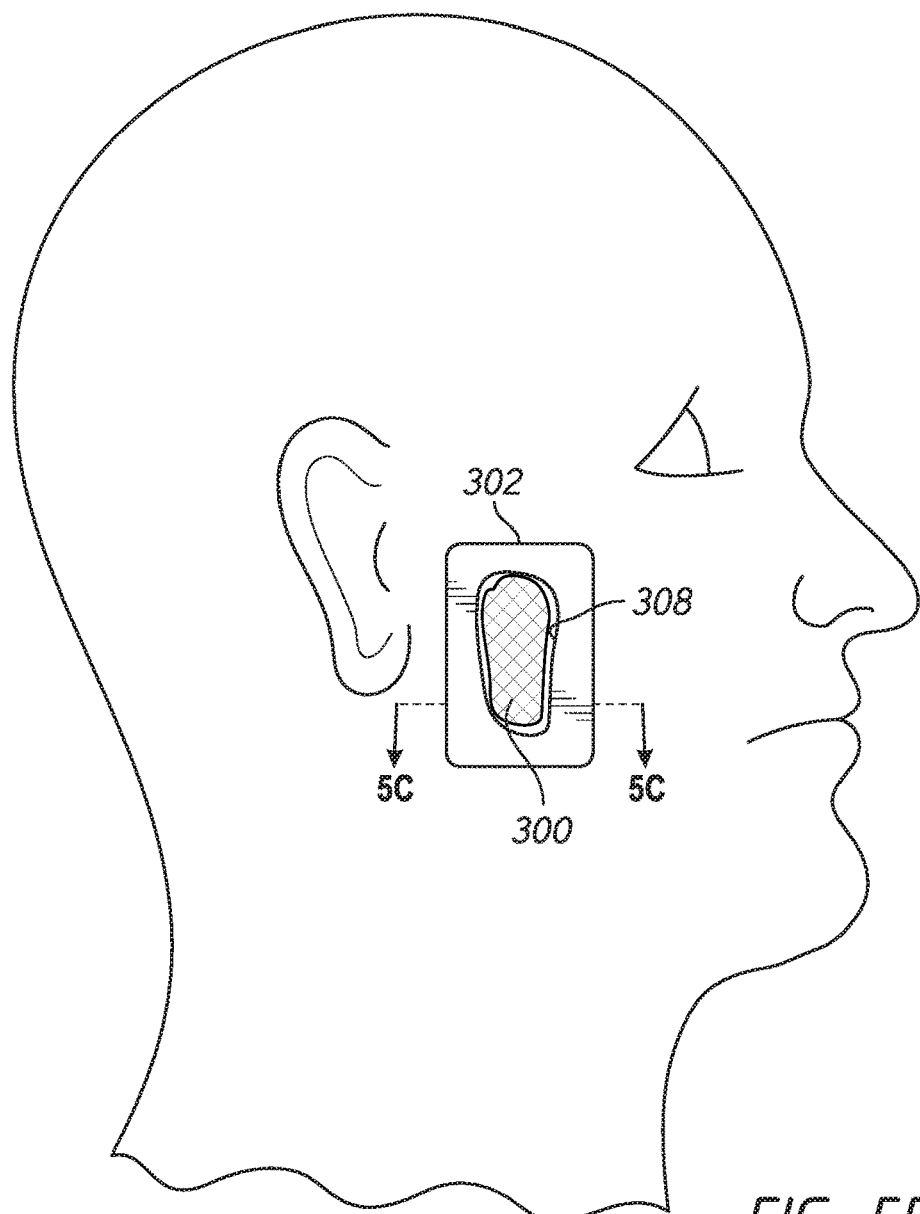
FIG. 5B shows the subject after a protective element has been applied.
Figure 5C:
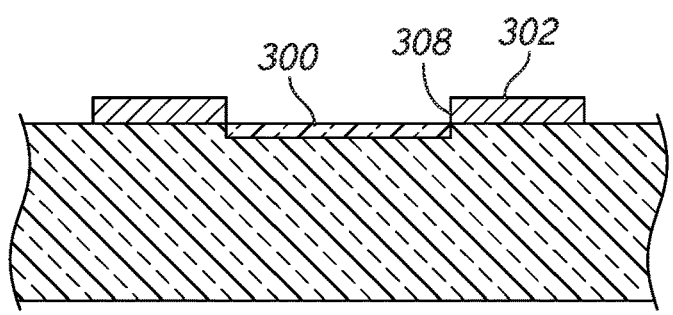
FIG. 5C is a schematic cross-sectional view of tissue and the applied protective element taken along line 5C-5C of FIG. 5B.
Figure 5D:
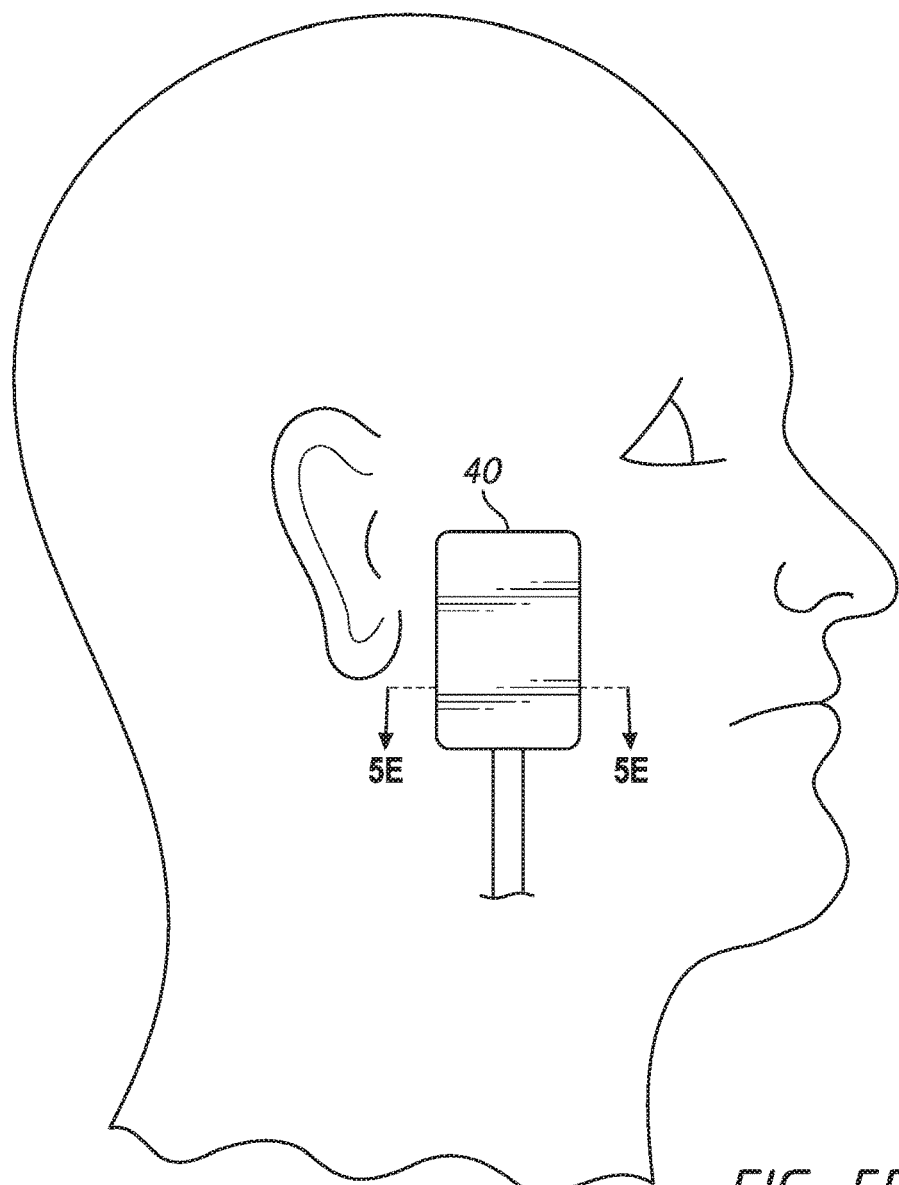
FIG. 5D shows an applicator applied to the protective element and the subject's skin.
Figure 5E:
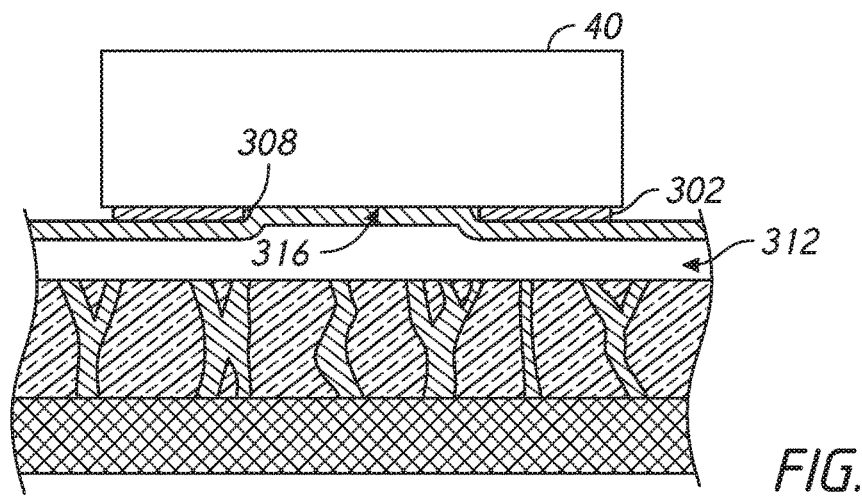
FIG. 5E is a schematic cross-sectional view of tissue, the protective element, and the applicator taken along line 5E-5E of FIG. 5D.

FIGS. 5A-5E show another method for treating a treatment region. FIG. 5A illustrates a facial vascular anomaly 300 that can be targeted in accordance with embodiments of the disclosure. FIGS. 5B and 5C show the treatment region after a protective element 302 has been applied to the subject. The protective element 302 can have an opening 308 formed to allow access to the vascular anomaly 300 and can be made, in whole or in part, of foam, rubber, or other thermally insulating material. A cryoprotectant can be applied to the exposed skin to help protect non-targeted tissues, such as the epidermis located at the opening 308. FIGS. 5D and 5E show an applicator 40 cooling tissue to affect the vascular anomaly 300. If the temperature-controlled surface area 316 is relatively large, the protective element 302 can inhibit cooling of the surrounding non-targeted tissue 312 and thereby localize cooling. In some embodiments, the protective element 302 is pre-loaded or otherwise carries cryoprotectant or other substance and can be an absorbent member, a pouch, etc. A separate element (e.g., an absorbent member with cryoprotectant, a pouch filled with cryoprotectant, etc.) can be placed within the opening 308. This allows for different compositions to be delivered to the treatment site and the surrounding tissue. In some embodiments, the protective element 302 can include one or more heaters, energy delivery elements, and/or other active elements that can periodically or continuously deliver energy to tissue (e.g., non-targeted tissue). Other techniques and components can be used to control heating/cooling, freeze injury, or the like.

Figure 6:
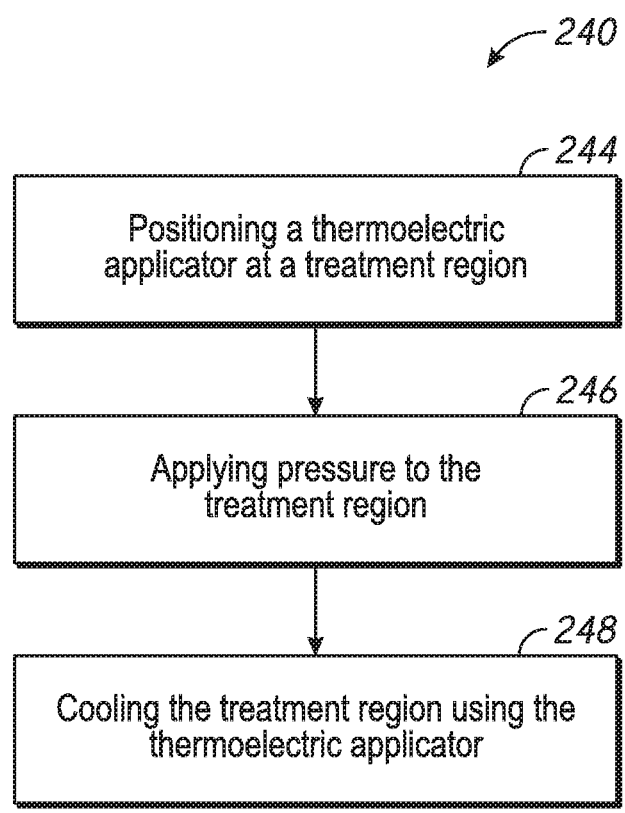
FIG. 6 is a flow diagram illustrating a method for treating a treatment site in accordance with embodiments of the technology.

FIG. 6 is a flow diagram illustrating a method 240 for improving the appearance of a subject in accordance with embodiments of the disclosure. Generally, an early stage of the method 240 can include applying a non-invasive cooling device to the surface of the subject's skin. The cooling device can be used to apply pressure to the treatment region to restrict blood flow in the vascular formation and to cool tissue. The cooling can substantially affect and injure the target vascular structure as discussed in connection with FIGS. 4A to 5E. Details of the method 240 are discussed below.

At block 244, an applicator (e.g., a thermoelectric applicator 40) is applied to the treatment region. The thermoelectric applicator 40 is positioned along the subject's skin surface to substantially cover a vascular formation and, in some procedures, covers at least about 50%, 60%, 70%, 80%, 90%, 95%, 99%, or 100% of the area of the vascular formation.

At block 246, the thermoelectric applicator can be used apply pressure to the treatment region. The applied pressure can be a constant or variable pressure that is sufficient to inhibit blood flow. In some procedures, the pressure can be applied before beginning a cooling cycle. The applicator 40 can include one or more openings through which a vacuum is drawn to pull the skin through the opening 308 and against the temperature-controlled surface area 316.

At block 248, the thermoelectric applicator can cool the skin surface to affect target structures to reduce or eliminate visible blood vessels and thereby reduce their visibility. The targeted structures can include, for example, arterial blood vessels, venous blood vessels, capillaries, vascular structures with abnormal characteristics (e.g., irregular shapes), a group of vessels, or the like. To treat port wine stains or other capillary vascular malformations, the targeted vascular structure can be a collection of ectatic vessels. To treat hemangioma or spider veins, the targeted vascular structure can be an abnormally dense collection of blood vessels (e.g., dilated blood vessels).

Without being bound by theory, the effect of cooling is believed to result in, for example, cell destruction, membrane disruption, cell shrinkage, disabling, damaging, removing, killing or other methods of cell alteration. Such alteration is believed to stem from one or more mechanisms acting alone or in combination. For example, cells of vascular structures (e.g., cells in blood vessel walls) can be destroyed via necrosis, apoptosis, or other suitable mechanism. Cold-induced vessel necrosis can be achieved during a cooling cycle. The temperature profile, cryoprotectant, and other treatment parameters can be used to selectively destroy abnormal vessels via necrosis. The damaged or destroyed vessels can be replaced with small arterioles and venules that are similar to the arterioles and venules located in surrounding normal skin. Additional treatments can be performed to target such new vessel structures due to revascularization. In cold-induced apoptosis procedures, blood vessels can be gradually destroyed after completing a cooling cycle. Apoptosis, also referred to as "programmed cell death" is a genetically-induced death mechanism by which cells self-destruct without causing damage to surrounding tissues.

In some embodiments, the skin surface can be cooled to a temperature lower than about −5° C. and higher than about −25° C. or −30° C. for a period of time sufficiently long to substantially affect a significant portion of the vascular formation. In some procedures, the period of time is sufficiently long to substantially injure a majority of blood vessels in the vascular formation. For example, at least 60%, 70%, 80%, 90%, and 95% of the total number of vessels that form the targeted vascular formation can be damaged or destroyed. The period of time can be about 1 minute to about 30 minutes, about 2 minutes to about 45 minutes, about 5 minutes to about 60 minutes or other period of time selected based on the treatment temperature profile. In certain treatments, the skin surface can be cooled to a temperature equal to or lower than about 10° C., 5° C., 0° C., −5° C., −10° C., −12° C., −15° C., −20° C., −30° C., or −35° C. for a period of time equal to or less than about 1 minute, 5 minutes, 10 minutes, 20 minutes, 30 minutes, 40 minutes, 50 minutes, 1 hour, 2 hours, or other suitable period of time. The patient may also experience a wound healing response, such as vessel recurrence that causes discoloration. Additional treatments can be performed to compensate for such wound healing response. Accordingly, any number of treatments can be performed to keep the number of working blood vessels at or below an threshold level. Repeatedly injuring vessels can result in permanent reduction of the functioning of blood vessels and, in some embodiments, the inhibition or prevention of body signaling that causes generation of blood vessels. Advantageously, the skin can be cooled while keeping pain or discomfort at or below an acceptable level.

Any number of treatment sessions can be performed to address post-treatment blood vessel recurrence because vessels may return as a result of angiogenesis. In some treatment plans, each treatment session can destroy a percentage of the total number of abnormal vessels. Multiple treatment sessions can be performed to destroy a desired amount of the abnormal vessels. In some procedures, substantially all of the abnormal vessels can be destroyed so that the treatment site has a normal appearance. The overall reduction in the number and/or size of the vessels can be selected to achieve a desired appearance.

Targeted features can be supercooled so as to not create any partial or total freeze event. Alternatively, a partial or total freeze event in a cooling zone (e.g., cooling zone 80 of FIG. 1) can be maintained by continuously or periodically cooling the patient's tissue to keep a target volume of targeted features at or below a treatment temperature. For example, a cryoprotectant can be used to inhibit or prevent freezing of non-targeted tissue. If the targeted features are in the epidermis, a cryoprotectant can be used to protect the dermis and deeper tissue. If the targeted features are in the dermis, a cryoprotectant can be used to protect the epidermis and/or deeper tissue. For example, a cryoprotectant can be used to protect the epidermis and another cryoprotectant can be used to protect the connective tissue and/or subcutaneous tissue.

The treatment site can be periodically or continuously monitored using the sensors (e.g., sensors 107 of FIG. 1). The sensors can be temperature sensors, pressure sensors, or other sensors capable of monitoring treatment. Temperature sensors can be thermistors, heat flux sensors, optical sensors, or the like. Optical sensors can be capable of detecting changes in the optical characteristics of tissue caused by treatment. Freezing of tissue can cause such optical changes. The optical sensor can include one or more energy emitters (e.g., light sources, light emitting diodes, etc.), detector elements (e.g., light detectors), or other components for non-invasively monitoring optical characteristics of tissue. In place of or in conjunction with monitoring using optical techniques, tissue can be monitored using electrical and/or mechanical techniques because changes in electrical impedance and/or mechanical properties of the tissue can be detected and may indicate tissue changes.

Real-time collection and processing of such feedback can be used in concert with treatment administration to effectively control cooling/heating of tissue. The sensor measurements can indicate other changes or anomalies that can occur during treatment administration. For example, an increase in temperature detected by one or more sensors can indicate a freezing event at the skin or underlying tissue (i.e., dermal tissue). An increase in temperature as detected by the sensors can also indicate movement associated with the thermoelectric applicator. Methods and systems for collection of feedback data and monitoring of temperature measurements are described in commonly assigned U.S. Pat. No. 8,285,390.

In some procedures, a controller (e.g., controller 114 of FIG. 2) is programmed to cause the applicator to detect the pressure applied to the subject and to control operation of the applicator based on the detected pressure. The sensors can be mechanical or optical pressure sensors capable of detecting the pressure applied to the subject's skin. If the pressure is reduced, blood flow into and through the treatment region can increase and tend to warm the target vascular structures. To counteract such warming, heat transfer rate from the subject's skin to the applicator can be increased. The temperature of the temperature-controlled surface (e.g., surface 102 of FIG. 1) can be increased or decreased to compensate for changes at the treatment region. In some procedures, the sensors 107 can be or include at least one temperature sensor and at least one pressure sensor. The controller can control operation of the thermoelectric applicator based on the detected temperature and pressure.

Suitable cryoprotectants and processes for implementing cryoprotectants are described in commonly assigned U.S. Patent Publication No. 2007/0255362. The cryoprotectant may additionally include a thickening agent, a pH buffer, a humectant, a surfactant, and/or other additives and adjuvants as described herein. Freezing point depressants may include, for example, propylene glycol (PG), polyethylene glycol (PEG), dimethyl sulfoxide (DMSO), or other suitable alcohol compounds. In a particular embodiment, a cryoprotectant may include propylene glycol, glycerin (a humectant), and ethanol. In another embodiment, a cryoprotectant may include propylene glycol, hydroxyethyl cellulose (a thickening agent), and water. In a further embodiment, a cryoprotectant may include polypropylene glycol, glycerin, and ethanol. The freezing point depressant may also include ethanol, propanol, iso-propanol, butanol, and/or other suitable alcohol compounds. Certain freezing point depressants (e.g., PG, PPG, PEG, etc.) may also be used to improve spreadability of the cryoprotectant and to provide lubrication. The freezing point depressant may lower the freezing point of tissue and/or body liquids/lipids to about 0° C. to −50° C., about 0° C. to −40° C., or about 0° C. to −30° C. In other embodiments, the freezing point of the liquids/lipids can be lowered to about −10° C. to about −40° C., about −10° C. to about −30° C., or about −10° C. to about −20° C. In certain embodiments, the freezing point of the liquids/lipids can be lowered to a temperature below about 0° C., −5° C., −10° C., −12° C., −15° C., −20° C., −30° C., or −35° C.

One expected advantage of at least some techniques disclosed herein is that the target vascular structure at the treatment region can be reduced generally without collateral damage to non-vascular tissue, shallower layer(s) of tissue, etc. at the same region. Multiple cryoprotectants can be used to protect different types of tissue. As a result, vascular tissue, blood, or other targeted tissue can be affected while other non-targeted tissue or cells in the same region are generally not damaged even though the non-targeted tissue or cells may be subjected to even lower temperatures than those to which the targeted tissue or cells are exposed.

E. Suitable Computing Environments

Figure 7:
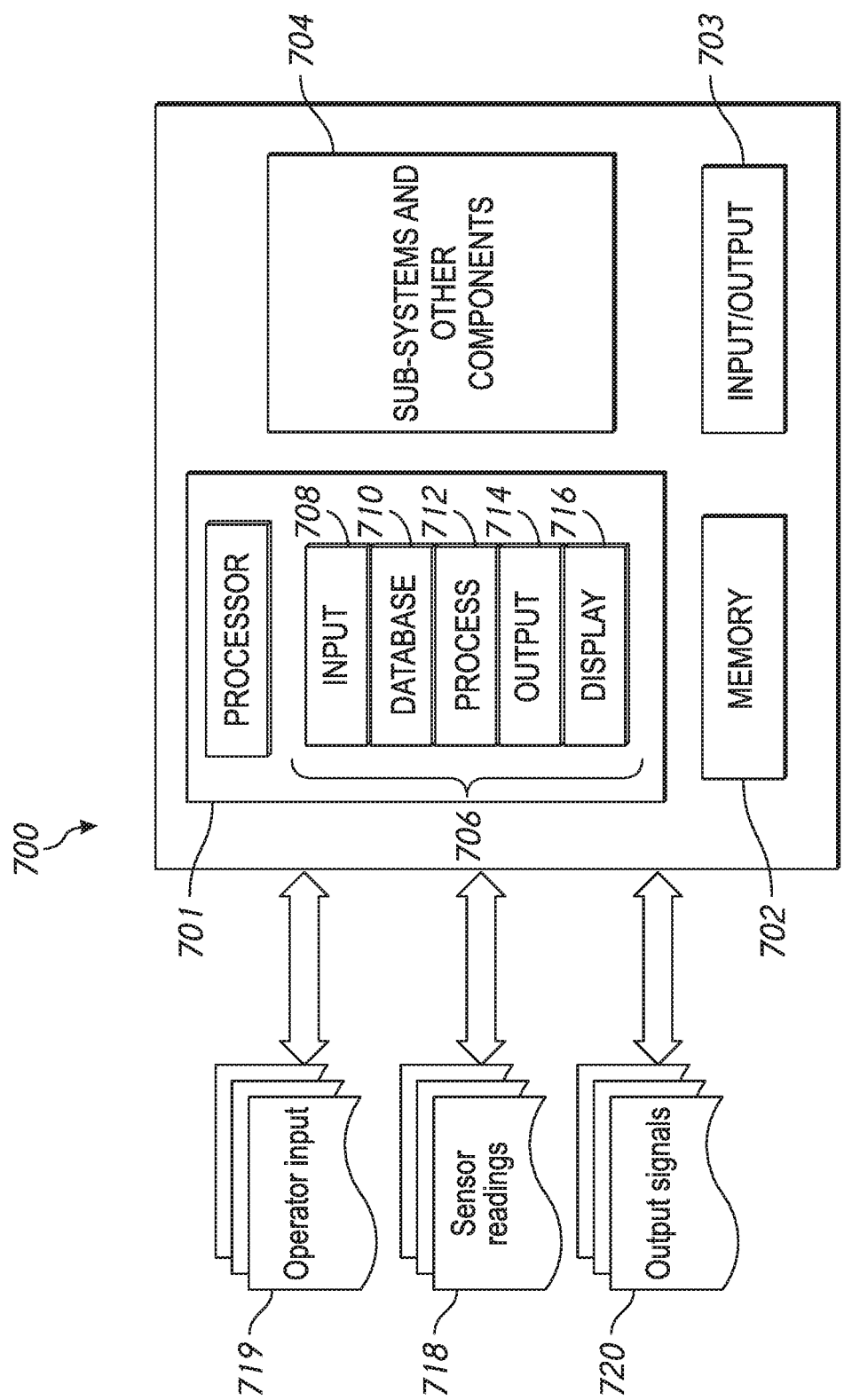
FIG. 7 is a schematic block diagram illustrating computing system software modules and subcomponents of a computing device suitable to be used in treatment systems in accordance with embodiments of the technology.

FIG. 7 is a schematic block diagram illustrating subcomponents of a controller in accordance with an embodiment of the disclosure. A controller or computing device 700 can be the controller 114 of FIG. 2 or can be incorporated into applicators (e.g., applicator 40 of FIGS. 1 and 2). The controller 700 can include a computing device having a processor 701, a memory 702, input/output devices 703, and/or subsystems and other components 704. The computing device 700 can perform any of a wide variety of computing processing, storage, sensing, imaging, and/or other functions. Components of the computing device 700 may be housed in a single unit or distributed over multiple, interconnected units (e.g., through a communications network). The components of the computing device 700 can accordingly include local and/or remote memory storage devices and any of a wide variety of computer-readable media.

As illustrated in FIG. 7, the processor 701 can include a plurality of functional modules 706, such as software modules, for execution by the processor 701. The various implementations of source code (i.e., in a conventional programming language) can be stored on a computer-readable storage medium or can be embodied on a transmission medium in a carrier wave. The modules 706 of the processor can include an input module 708, a database module 710, a process module 712, an output module 714, and, optionally, a display module 716.

In operation, the input module 708 accepts an operator input 719 (e.g., characteristics of wrinkles, location of wrinkles, etc.) via the one or more input devices, and communicates the accepted information or selections to other components for further processing. The database module 710 organizes records, including patient records, treatment data sets, treatment profiles and operating records, and other operator activities; and it facilitates storing and retrieving of these records to and from a data storage device (e.g., internal memory 702, an external database, etc.). Any type of database organization can be utilized, including a flat file system, hierarchical database, relational database, distributed database, etc.

In the illustrated example, the process module 712 can generate control variables based on sensor readings 718 from sensors (e.g., sensors 107 of FIG. 1) and/or other data sources, and the output module 714 can communicate operator input to external computing devices and control variables to the controller. The display module 716 can be configured to convert and transmit processing parameters, sensor readings 718, output signals 720, input data, treatment profiles and prescribed operational parameters through one or more connected display devices, such as a display screen, printer, speaker system, etc.

In various embodiments, the processor 701 can be a standard central processing unit or a secure processor. Secure processors can be special-purpose processors (e.g., a reduced instruction set processor) that can withstand sophisticated attacks that attempt to extract data or programming logic. The secure processors may not have debugging pins that enable an external debugger to monitor the secure processor's execution or registers. In other embodiments, the system may employ a secure field programmable gate array, a smartcard, or other secure devices.

The memory 702 can be standard memory, secure memory, or a combination of both memory types. By employing a secure processor and/or secure memory, the system can ensure that data and instructions are highly secure and that sensitive operations such as decryption are shielded from observation. In various embodiments, the memory 702 can be flash memory, secure serial EEPROM, a secure field programmable gate array, or a secure application-specific integrated circuit. The memory 702 can store treatment plans or protocols, executable instructions (e.g., instructions executable by the processor 701), etc. In some procedures, the memory has instructions for commanding the thermoelectric applicator to perform the treatment protocol, or protocols, requested by the user. The user interface (e.g., input/output device 118 of FIG. 2 or input/output device 703 of FIG. 7) communicates with the controller to enable a user to request one of the treatment protocols. The treatment protocols include one or more blood vessel treatment protocols, vascular malformation treatment protocols, port wine stain treatment protocols, and/or capillary vessel treatment protocols. Each protocol can include treatment periods, temperature profiles, etc. for achieving a desired effect.

The effects of the treatment can be evaluated using subjective and/or objective methods. Subjective evaluations can be performed by visually inspecting the treatment region. Objective evaluations can be performed using laser Doppler (e.g., laser Doppler flowmetry), reflectance spectrometry, reflectance confocal microscopy, tristimulus colorimetry, cross-polarized diffuse reflectance, and/or various known techniques for qualitatively assessing the subject's tissue. In some procedures, qualitatively assessments can be performed to evaluate areas with vascular formations and a wide range of effects to vascular formations (e.g., when the formation is substantially affected and injured, percentage of destroyed vascular structures, area occupied by vascular formation, etc.). A multisession treatment protocol can be updated based on the evaluation to refine treatments. The systems disclosed herein or separate systems can be used to evaluate subjects. For example, applicators can have components for evaluating the treatment region before, during, and/or after the session. The configuration, components, and functionality of the applicators can be selected based on the desired evaluation.

The input/output device 118 can include, without limitation, a keyboard, a mouse, a stylus, a push button, a switch, a potentiometer, a scanner, an audio component such as a microphone, or any other device suitable for accepting user input, and can also include one or more video monitors, medium readers, audio devices such as a speaker, any combination thereof, and any other device or devices suitable for providing user feedback. For example, if the applicator 40 moves an undesirable amount during a treatment session, the input/output device 703 can alert the subject 103 (FIG. 2) and/or operator via an audible alarm. The input/output device (e.g., input/output device 118 of FIG. 2) can be a touch screen that functions as both an input device and an output device. The control panel can include visual indicator devices or controls (e.g., indicator lights, numerical displays, etc.) and/or audio indicator devices or controls. The control panel may be a component separate from the input and/or output device, may be integrated with one or more of the devices, may be partially integrated with one or more of the devices, may be in another location, and so on. In alternative embodiments, the controller can be contained in, attached to, or integrated with the cooling devices and applicators disclosed herein. In yet other embodiments, the various components can be fixedly installed at a treatment site. Further details with respect to components and/or operation of applicators, control modules (e.g., treatment units), and other components may be found in commonly assigned U.S. Patent Publication No. 2008/0287839.

The controller 700 can include any processor, Programmable Logic Controller, Distributed Control System, secure processor, and the like. A secure processor can be implemented as an integrated circuit with access-controlled physical interfaces, tamper resistant containment, means of detecting and responding to physical tampering, secure storage, and shielded execution of computer-executable instructions. Some secure processors also provide cryptographic accelerator circuitry. Suitable computing environments and other computing devices and user interfaces are described in commonly assigned U.S. Pat. No. 8,275,442, entitled "TREATMENT PLANNING SYSTEMS AND METHODS FOR BODY CONTOURING APPLICATIONS," which is incorporated herein in its entirety by reference. The instructions can be for causing an applicator to cool the subject's skin to a temperature or temperature range for a predetermined period of time. The controller can store treatment plans corresponding to different types of targeted features and desired outcomes. Each treatment plan can include treatment parameters, such as threshold applied pressure, treatment temperature(s), cooling/heating periods, etc. The input/output device 118 of FIG. 2 can be used to select a treatment plan for a particular treatment site. For example, the controller 114 can store and execute different treatment plans for treating port wine stains at various locations along the patient's body. In some embodiments, the controller 700 is configured to receive output from a sensor (e.g., sensor 107 in FIG. 1) and to cause the thermoelectric cooler to continue to cool the surface of the subject's skin for a period of time after the sensor detects at least partial freezing of skin tissue. The period of time of further cooling can be 1 minute, 5 minutes, 10 minutes, or the like.

The controller 700 can store, determine, and/or monitor thermal cycles for sequentially cooling and heating a treatment site any number of times. The controller 700 can select the order and lengths of thermal cycles (e.g., heating cycles, cooling cycles, etc.), target parameters (e.g., temperatures, temperature ranges, etc.), and/or temperature profiles. After cooling, cooling devices can be actively or passively warmed to room temperature, skin temperature, or another suitable temperature. For example, the thermoelectric elements of the cooling devices can be passively (e.g., naturally) returned to room temperature before the applicator is removed from the subject.

The applicators in some embodiments can deliver energy (e.g., radiofrequency energy, ultrasound energy, etc.) to and remove heat from the target region. The application can be selected based on the treatment site of the subject, which can be human or other mammalian animal. A session may have a single stage of delivering energy that ceases prior to a single stage of removing heat from target nerve tissue. Additionally, sequential application of the stages of heating or cooling may occur multiple times so that multiple non-overlapping stages of energy delivery and heat removal occur. For example, thermal elements of an applicator can perform a heating cycle while other thermal elements of the applicator perform a cooling cycle. The controller 700 can store various executable programs for controlling applicators disclosed herein to perform a wide range of thermal cycles for blood vessel alteration, body contouring, treating cellulite, improving skin appearance, targeting glands, and/ or performing other methods as described in, for example, U.S. patent application Ser. No. 14/611,127 entitled "TREATMENT SYSTEMS, METHODS, AND APPARATUS FOR IMPROVING THE APPEARANCE OF SKIN AND PROVIDING FOR OTHER TREATMENTS", U.S. patent application Ser. No. 14/611,052 entitled "TREATMENT SYSTEMS AND METHODS FOR TREATING CELLULITE AND FOR PROVIDING OTHER TREATMENTS," and International Patent Application No. PCT/US2015/013,971 entitled "TREATMENT SYSTEMS AND METHODS FOR AFFECTING GLANDS AND OTHER TARGETED STRUCTURES," which are incorporated herein in their entireties by reference.

Different types of cooling techniques can be used to thermally affect targeted structures. For example, treatment systems and devices are disclosed herein to control thermal parameters such that tissue body fluids within the treatment site are supercooled to temperatures below the freezing point without forming or nucleating ice crystals so that a non-freezing treatment results. Alternatively or additionally, after a supercooling state exists, the supercooled tissue/body fluids can then be intentionally nucleated to create a freeze zone and to damage, reduce, disrupt, or otherwise affect the targeted cells or structures. Nucleation can be induced by delivering an alternating current to the tissue, applying a nucleating solution onto the surface of the skin (e.g., one that includes bacteria which initiate nucleation), and/or by creating a mechanical perturbation to the tissue, such as by use of vibration, ultrasound energy, etc. In some procedures, the surface of the subject's skin can be cooled to create a supercooled cooling zone that includes the target structure. The surface of the subject's skin can then be heated to warm non-targeted shallow tissue while the nerve tissue and/or surrounding body fluid remain in supercooled states. Nucleation can then be induced in the localized supercooled region without substantially freezing or altering the warmed shallow tissue. The controller 700 can store various executable programs for controlling applicators disclosed herein to perform these techniques.

F. Conclusion

Various embodiments of the technology are described above. It will be appreciated that details set forth above are provided to describe the embodiments in a manner sufficient to enable a person skilled in the relevant art to make and use the disclosed embodiments. Furthermore, features, structures, or characteristics of various embodiments may be combined in any suitable manner. For example, embodiments disclosed herein can be used with techniques, methods, compositions, devices, and systems disclosed in U.S. Pat. No. 7,367,341 entitled "METHODS AND DEVICES FOR SELECTIVE DISRUPTION OF FATTY TISSUE BY CONTROLLED COOLING" to Anderson et al. and U.S. Patent Publication No. 2005/0251120 entitled "METHODS AND DEVICES FOR DETECTION AND CONTROL OF SELECTIVE DISRUPTION OF FATTY TISSUE BY CONTROLLED COOLING" to Anderson et al., the entire disclosures of which are incorporated herein by reference. Moreover, one skilled in the art will recognize that there are a number of other technologies that could be used to perform functions similar to those described above. While processes or blocks are presented in a given order, alternative embodiments may perform routines having stages, or employ systems having blocks, in a different order, and some processes or blocks may be deleted, moved, added, subdivided, combined, and/or modified. Each of these processes or blocks may be implemented in a variety of different ways. Also, while processes or blocks are at times shown as being performed in series, these processes or blocks may instead be performed in parallel, or may be performed at different times. The headings provided herein are for convenience only and should not be used to interpret the scope or meaning of the described technology.

Unless the context clearly requires otherwise, throughout the description, the words "comprise," "comprising," and the like are to be construed in an inclusive sense, as opposed to an exclusive or exhaustive sense; that is to say, in a sense of "including, but not limited to." Words using the singular or plural number also include the plural or singular number, respectively. Use of the word "or" in reference to a list of two or more items covers all of the following interpretations of the word: any of the items in the list, all of the items in the list, and any combination of the items in the list. Furthermore, the phrase "at least one of A, B, and C, etc." is intended in the sense that one having ordinary skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense that one having ordinary skill in the art would understand the convention (e.g., "a system having at least one of A, B, or C" would include but not be limited to systems that have A alone, B alone, C alone, A and B together, A and C together, B and C together, and/or A, B, and C together, etc.).

Any patents, applications and other references, including any that may be listed in accompanying filing papers, are incorporated herein by reference. Aspects of the described technology can be modified, if necessary, to employ the systems, functions, and concepts of the various references described above to provide yet further embodiments. These and other changes can be made in light of the above Detailed Description. While the above description lists certain embodiments and describes the best mode contemplated, no matter how detailed the description, various changes can be made. Implementation details may vary considerably, while still being encompassed by the technology disclosed herein. As noted above, particular terminology used when describing certain features or aspects of the technology should not be taken to imply that the terminology is being redefined herein to be restricted to any specific characteristics, features, or aspects of the technology with which that terminology is associated. The various aspects and embodiments disclosed herein are for purposes of illustration and are not intended to be limiting, with the true scope and spirit being indicated by the following claims.

What is claimed is:

1. A method for affecting a target vascular structure at a treatment region of a subject's skin surface having a target area and a non-target area, comprising:
applying a thermoelectric applicator to the treatment region such that the thermoelectric applicator overlays the target area of the skin surface and the non-target area of the skin surface; and
noninvasively cooling the target area of the skin surface to a temperature low enough and for a period of time long enough using the thermoelectric applicator so as to substantially affect and injure the target vascular structure while selectively protecting the non-targeted area of the skin surface, which surrounds the target vascular structure and underlies the thermoelectric applicator, from being affected by the cooling of the skin surface, and wherein the target vascular structure includes blood vessels, vascular malformations, port wine stains, and/or capillary vessels.

2. The method of claim 1, wherein the thermoelectric applicator is applied over the treatment region with sufficient pressure to substantially limit blood flow in the target vascular structure such that the target vascular structure is more effectively affected and injured by the low temperature.

3. The method of claim 2, wherein the skin surface is cooled to the temperature, which is less than −5° C. and greater than −25° C. or −30° C. for 2 minutes to 20 minutes such that the target vascular structure is cooled sufficiently to produce a freeze injury thereto and to substantially affect and injure a majority of blood vessels in the target vascular structure.

4. The method of claim 1, wherein applying the thermoelectric applicator to the treatment region includes:
  locating the target vascular structure; and
  positioning the thermoelectric applicator at the treatment region based on a location of the target vascular structure, and wherein the target vascular structure occupies more than either 50%, 60%, 70%, 80%, 90%, or 99% of an area of the treatment region.

5. The method of claim 1, wherein applying the thermoelectric applicator to the treatment region includes positioning a cooling surface of the thermoelectric applicator over a majority of the vascular formation, and wherein the cooling surface has an area equal to or larger than about either 2, 3, 4, 5, 6, 7, 8, 9, 10, 12, 15, 20, or 25 cm².

6. A method for affecting a vascular formation in a skin surface of the subject, comprising:
  positioning a non-invasive thermoelectric cooling applicator along the skin surface of the subject based on a position of the vascular formation such that a cooling surface of the non-invasive thermoelectric cooling applicator substantially covers the vascular formation and the vascular formation occupies more than 50% of a skin surface area covered by the cooling surface;
  selecting a target region of the skin surface area covered by the cooling surface and corresponding to the vascular formation;
  protecting a non-targeted region of the subject's skin that is covered by the cooling surface and surrounds the target region;
  applying pressure to the thermoelectric cooling applicator so as to restrict blood flow in the vascular formation; and
  cooling the selected target region of the skin surface area using the non-invasive thermoelectric cooling applicator such that the selected target region is at a temperature lower than −5° C. and higher than −25° C. or −30° C. for a period of time sufficiently long to substantially affect the vascular formation without substantially affecting non-targeted skin tissue at the non-targeted region underlying the cooling surface and surrounding the vascular formation, wherein the vascular formation is blood vessels, vascular malformations, port wine stains, and/or capillary vessels.

7. The method of claim 6, wherein the period of time is 2 minutes to 20 minutes.

8. The method of claim 6, wherein positioning the non-invasive thermoelectric cooling applicator along the subject's skin surface includes:
  applying a temperature-controlled surface of the non-invasive thermoelectric cooling applicator over the vascular formation, and wherein the temperature-controlled surface has an area equal to or larger than either 2, 3, 4, 5, 6, 7, 8, 9, 10, 12, 15, 20 or 25 cm².

9. The method of claim 6, further comprising using a control unit that controls a temperature of the thermoelectric cooling applicator and a length of time the skin surface is cooled such that the vascular formation is substantially affected and injured.

10. The method of claim 6, further comprising applying sufficient pressure to the vascular formation using the thermoelectric cooling applicator to restrict blood flow in the vascular formation such to enhance the effect to the vascular formation caused by the cooling of the skin.

11. The method of claim 6, further comprising controlling the thermoelectric cooling applicator to provide a temperature and a treatment time such that a significant number of blood vessels in the vascular formation are injured to an extent to substantially reduce blood flow therethrough after a day following a treatment and a majority of capillary vessels are damaged while doing minimal injury to other skin structures outside of the vascular formation.

12. The method of claim 6, further comprising using at least one of a cryoprotectant or a protective element to protect the non-targeted skin tissue, wherein the protective element comprises a thermally insulating material.

13. The method of claim 6, further comprising:
  applying material to the skin surface at the non-targeted region while leaving the skin surface at the selected target region unprotected,
  wherein the selected target region and the non-target region are concurrently cooled by the cooling surface.

14. A method for affecting a target vascular structure at a treatment region of a subject's skin, comprising:
  identifying a target area and a non-target area of the treatment region of a subject's skin;
  shaping a protective element based on the identification of the target area of the treatment region;
  applying the protective element to the treatment region such that the protective element exposes the target area and overlays the non-target area, and
  applying a thermoelectric applicator to the protective element and the target area such that the protective element is directly between the thermoelectric applicator and the non-targeted tissue, wherein the protective element inhibits heat transfer between the non-targeted tissue and the thermoelectric applicator to prevent thermal injury to the non-targeted tissue while the applicator noninvasively cools the target area of the skin surface to a temperature less than −5° C. and greater than −25° C. or −30° C., wherein the target vascular structure is blood vessels, vascular malformations, port wine stains, and/or capillary vessels.

* * * * *